(12) United States Patent
Zhou et al.

(10) Patent No.: US 11,691,132 B2
(45) Date of Patent: Jul. 4, 2023

(54) MODIFIED Y-TYPE MOLECULAR SIEVE, CATALYTIC CRACKING CATALYST COMPRISING THE SAME, THEIR PREPARATION AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Lingping Zhou, Beijing (CN); Qiuqiao Jiang, Beijing (CN); Shuai Yuan, Beijing (CN); Hao Sha, Beijing (CN); Mingde Xu, Beijing (CN); Zhenyu Chen, Beijing (CN); Weilin Zhang, Beijing (CN); Huiping Tian, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 284 days.

(21) Appl. No.: 17/268,679

(22) PCT Filed: Aug. 15, 2019

(86) PCT No.: PCT/CN2019/100733
§ 371 (c)(1),
(2) Date: Feb. 16, 2021

(87) PCT Pub. No.: WO2020/035016
PCT Pub. Date: Feb. 20, 2020

(65) Prior Publication Data
US 2021/0170372 A1   Jun. 10, 2021

(30) Foreign Application Priority Data

Aug. 17, 2018 (CN) .......................... 201810940921.4
Aug. 17, 2018 (CN) .......................... 201810942057.1

(51) Int. Cl.
| | | |
|---|---|---|
| B01J 29/08 | (2006.01) | |
| B01J 21/04 | (2006.01) | |
| B01J 21/16 | (2006.01) | |
| B01J 35/10 | (2006.01) | |
| B01J 37/10 | (2006.01) | |
| B01J 37/30 | (2006.01) | |
| C07C 4/06 | (2006.01) | |
| C10G 11/05 | (2006.01) | |

(52) U.S. Cl.
CPC ............. *B01J 29/088* (2013.01); *B01J 21/04* (2013.01); *B01J 21/16* (2013.01); *B01J 35/1038* (2013.01); *B01J 35/1061* (2013.01); *B01J 35/1066* (2013.01); *B01J 37/10* (2013.01); *B01J 37/30* (2013.01); *C07C 4/06* (2013.01); *C10G 11/05* (2013.01); *B01J 2229/186* (2013.01); *B01J 2229/24* (2013.01); *B01J 2229/36* (2013.01); *B01J 2229/37* (2013.01); *C07C 2521/04* (2013.01); *C07C 2521/16* (2013.01); *C07C 2529/08* (2013.01); *C10G 2300/202* (2013.01); *C10G 2300/308* (2013.01); *C10G 2400/30* (2013.01)

(58) Field of Classification Search
CPC . B01J 29/088; B01J 21/04; B01J 21/16; B01J 35/1038; B01J 35/1061; B01J 35/1066; B01J 37/10; B01J 37/30; B01J 2229/186; B01J 2229/24; B01J 2229/36; B01J 2229/37; C07C 4/06; C07C 2521/04; C07C 2521/16; C07C 2529/08; C10G 11/05; C10G 2300/202; C10G 2300/308; C10G 2400/30; C01B 39/24
See application file for complete search history.

(56) References Cited

U.S. PATENT DOCUMENTS

| | | | | |
|---|---|---|---|---|
| 2004/0266608 | A1* | 12/2004 | Long ...................... | C10G 11/05 502/64 |
| 2005/0133419 | A1* | 6/2005 | Long ...................... | C10G 11/05 208/120.25 |

(Continued)

FOREIGN PATENT DOCUMENTS

| | | |
|---|---|---|
| CN | 1026217 C | 10/1994 |
| CN | 1317359 C | 5/2007 |
| CN | 102049302 A | 5/2011 |
| CN | 102806098 A | 12/2012 |
| CN | 102806099 A | 12/2012 |
| CN | 103787352 A | 5/2014 |
| CN | 103923698 A | 7/2014 |
| CN | 103100417 B | 1/2015 |
| CN | 104560185 A | 4/2015 |
| CN | 104560187 A | 4/2015 |
| CN | 106140254 A | 11/2016 |
| CN | 106145152 A | 11/2016 |
| CN | 106145153 A | 11/2016 |

(Continued)

*Primary Examiner* — Ali Z Fadhel
(74) *Attorney, Agent, or Firm* — Novick, Kim & Lee, PLLC; Allen Xue

(57) ABSTRACT

A modified Y-type molecular sieve has a rare earth content of about 4% to about 11% by weight on the basis of the oxide, a phosphorus content of about 0.05% to about 10% by weight on the basis of $P_2O_5$, a sodium content of no more than about 0.5% by weight on the basis of sodium oxide, a gallium content of about 0.1% to about 2.5% by weight on the basis of gallium oxide, and a zirconium content of about 0.1% to about 2.5% by weight on the basis of zirconia; and the modified Y-type molecular sieve has a total pore volume of about 0.36 mL/g to about 0.48 mL/g, a percentage of the pore volume of secondary pores having a pore size of 2-100 nm to the total pore volume of about 20% to about 40%.

21 Claims, No Drawings

(56) References Cited

U.S. PATENT DOCUMENTS

| | | | |
|---|---|---|---|
| 2005/0279670 A1* | 12/2005 | Long | C10G 11/05 208/120.25 |
| 2007/0293714 A1 | 12/2007 | Long et al. | |
| 2010/0230324 A1* | 9/2010 | Al-Alloush | C10G 11/18 208/82 |
| 2014/0021098 A1 | 1/2014 | Kumar et al. | |

FOREIGN PATENT DOCUMENTS

| | | |
|---|---|---|
| CN | 106276961 A | 1/2017 |
| CN | 107973315 A | 5/2018 |
| CN | 108452830 A | 8/2018 |
| CN | 108452832 A | 8/2018 |
| CN | 108452833 A | 8/2018 |
| WO | 2013060099 A1 | 5/2013 |

* cited by examiner

MODIFIED Y-TYPE MOLECULAR SIEVE, CATALYTIC CRACKING CATALYST COMPRISING THE SAME, THEIR PREPARATION AND APPLICATION THEREOF

CROSS-REFERENCE TO RELATED APPLICATIONS

The present application is a US national phase entry of International Application No. PCT/CN2019/100733, filed on Aug. 15, 2019, which claims the priority of the patent application No. 201810940921.4 filed on Aug. 17, 2018 before the Chinese Patent Office, entitled "Modified Y-type molecular sieve, its preparation and application thereof", and the priority of the patent application No. 201810942057.1 filed on Aug. 17, 2018 before the Chinese Patent Office, entitled "Catalyst cracking catalyst, its preparation and application thereof", which are hereby incorporated by reference in their entireties.

TECHNICAL FIELD

The present application relates to the field of molecular sieves and catalytic cracking, and more particularly to a modified Y-type molecular sieve, a catalytic cracking catalyst comprising the same, their preparation, and application thereof.

BACKGROUND ART

Light aromatics such as benzene, toluene and xylene (BTX) are important basic organic chemical raw materials, which are widely used in the production of polyesters, chemical fibers, etc., and there is a very strong demand of them in recent years. Light aromatics such as benzene, toluene and xylene (BTX) are mainly derived from catalytic reforming and steam cracking processes using naphtha as raw materials. Due to the shortage of naphtha raw materials, there is a large market gap in light aromatics.

Catalytic cracking light cycle oil (LCO) is an important by-product of catalytic cracking. It is produced in large quantity and rich in aromatics, especially polycyclic aromatics, and is an inferior diesel fraction. With the development of market demand and environmental protection requirements, LCO is greatly restricted as a diesel blending component. The hydrocarbon composition of LCO includes paraffins, naphthenes (including a small amount of olefins) and aromatics. With different catalytic cracking feedstocks and operating severity, the hydrocarbon composition of LCO may be quite different. A main component of LCO is aromatics, which may account for a mass fraction of greater than 70%, or even about 90%, and the rest are paraffins and naphthenes. Bicyclic aromatics, as a component having the highest content in LCO, are a typical component of LCO, and are a key component affecting the production of light aromatics by catalytic cracking. Under catalytic cracking conditions, polycyclic aromatics are hard to be converted into light aromatics via ring-opening cracking. Under hydrogenation conditions, polycyclic aromatics are more easily to be saturated into heavy monocyclic aromatics, such as alkylbenzenes and cycloalkylbenzenes (e.g. indenes, tetrahydronaphthalenes, and indenes). Such heavy monocyclic aromatics are potential components for the production of light aromatics via catalytic cracking, and can be cracked into light aromatics under catalytic cracking conditions. Therefore, LCO is a potential and inexpensive resource for the production of light aromatics. The production of light aromatics through hydrogenation-catalytic cracking technology has important value in research.

In the prior arts of Chinese Patent Application Publication Nos. CN103923698A, CN104560185A, and CN104560187A, LCO is first subjected to moderate hydrogenation, in which most of the polycyclic aromatics are saturated into hydrogenated aromatics having a cycloalkane ring and an aromatic ring, and then to cracking reaction in the presence of a catalytic cracking catalyst to produce BTX light aromatics. However, the hydrogenated aromatics obtained by the hydrogenation of LCO are poorer in cracking ability, but much higher in hydrogen transfer ability than conventional catalytic cracking feedstocks. Therefore, conventional catalytic cracking catalysts used in the prior art cannot satisfy the requirement of the catalytic cracking of hydrogenated LCOs.

Since its first use in the 1960s, Y-type molecular sieves have been the main active component of fluid catalytic cracking (FCC) catalysts. However, as crude oils become heavier, the content of polycyclic compounds in FCC feedstocks increases significantly, while their ability to diffuse in the pores of molecular sieves decreases significantly. When catalysts comprising Y-type molecular sieves as the main active component are directly used to process heavy fractions such as residual oils, the accessibility of the active center of the catalysts will become a major obstacle to the cracking of polycyclic compounds contained therein, since Y-type molecular sieves used as the main active component have a pore size of only 0.74 nm. The pore structure of molecular sieves is closely related to the cracking performance, especially for residue cracking catalysts. Secondary pores of molecular sieves can increase the accessibility of macromolecules of residual oils to the active center of catalysts, thereby improving their cracking capability for residual oils.

Hydrothermal dealuminization method is one of the most widely used methods for preparing ultra-stable molecular sieves in the industry. The method comprises firstly subjecting a NaY molecular sieve to ion-exchange with an aqueous solution containing ammonium ions to reduce the content of sodium ion in the molecular sieve, and then subjecting the ammonium ion-exchanged molecular sieve to roasting at 600-825° C. in steam atmosphere to allow it to be ultra-stabilized. The method is cost-effective and is easy to be industrialized for large-scale production, and the ultra-stable Y-type molecular sieve thus obtained is rich in secondary pores, but there is a serious loss in the crystallinity of the ultra-stable Y-type molecular sieve.

At present, the production for ultra-stable Y-type molecular sieves used in the industry is normally based on an improvement on the above-mentioned hydrothermal roasting method. A method comprising two ion-exchange stages and two roasting stages can be adopted, which aims at solving the problem of severe loss of crystallinity encountered when roasting under severe conditions by carrying out the roasting in separate stages under milder conditions. The ultra-stable Y molecular sieve thus obtained may have a certain amount of secondary pores, but the proportion of secondary pores having a relatively large pore size in the total secondary pores is low. Besides, the specific surface area and the crystallinity of the ultra-stable molecular sieves also need to be further improved.

In order to better meet the need for the production of more BTX light aromatics via catalytic cracking of hydrogenated LCOs, the object of the present application is to develop a highly stable modified molecular sieve having a high cracking activity and a relatively lower hydrogen transfer capacity as a new active component, and further develop a catalytic cracking catalyst suitable for use in the catalytic cracking of hydrogenated LCOs for producing more BTX light aromatics based on this new active component, so as to promote the cracking reaction, control the hydrogen transfer reaction, further improve the conversion efficiency of hydrogenated LCOs, and maximize the production of catalytic gasolines rich in benzene, toluene and xylene (BTX).

SUMMARY OF THE INVENTION

An object of the present application is to provide a modified Y-type molecular sieve, a catalytic cracking catalyst comprising the same, their preparation and application thereof, so that catalytic cracking catalysts prepared by using the modified Y-type molecular sieve as an active component show a higher hydrogenated LCO conversion efficiency, a better coke selectivity and a higher yield of BTX-rich gasoline.

In order to achieve the above object, in an aspect, the present application provides a modified Y-type molecular sieve, having a rare earth content of about 4% to about 11% by weight on the basis of the oxide, a phosphorus content of about 0.05% to about 10% by weight on the basis of $P_2O_5$, a sodium content of no more than about 0.5% by weight on the basis of sodium oxide, a gallium content of about 0.1% to about 2.5% by weight on the basis of gallium oxide, and a zirconium content of about 0.1% to about 2.5% by weight on the basis of zirconia, based on the weight of the modified Y-type molecular sieve on a dry basis; wherein the modified Y-type molecular sieve has a total pore volume of about 0.36 mL/g to about 0.48 mL/g, a percentage of the pore volume of secondary pores having a pore size of 2-100 nm to the total pore volume of about 20% to about 40%; a lattice constant of about 2.440 nm to about 2.455 nm, a lattice collapse temperature of not lower than about 1060° C., a percentage of non-framework aluminum content to the total aluminum content of no more than about 10%, and a ratio of B acid to L acid in the strong acid content of the modified Y-type molecular sieve of no less than about 3.5.

In another aspect, the present application provides a method for the preparation of a modified Y-type molecular sieve, comprising the steps of:

(1) contacting a NaY molecular sieve with a rare earth salt solution for ion-exchange reaction, to obtain an ion-exchanged molecular sieve;

(2) subjecting the ion-exchanged molecular sieve to roasting at a temperature of about 350° C. to about 480° C. in an atmosphere comprising about 30 vol % to about 90 vol % of steam for about 4.5 hours to about 7 hours, to obtain a molecular sieve undergone a mild hydrothermal ultra-stabilization treatment;

(3) subjecting the molecular sieve undergone a mild hydrothermal ultra-stabilization treatment to gas phase ultra-stabilization by contacting and reacting with gaseous $SiCl_4$, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification by contacting with a phosphorus compound, to obtain a phosphorus-modified molecular sieve; and (6) subjecting the phosphorus-modified molecular sieve to a modification treatment by contacting with gallium and zirconium in a solution, and then to calcination, to obtain the modified Y-type molecular sieve.

In another aspect, the present application provides a catalytic cracking catalyst, comprising about 10% to about 50% by weight of a modified Y-type molecular sieve, about 10% to about 40% by weight of an alumina binder calculated on the basis of alumina, and about 10% to about 80% by weight on a dry basis of clay, based on the weight of the catalyst on a dry basis, wherein the modified Y-type molecular sieve is a modified Y-type molecular sieve according to the present application or a modified Y-type molecular sieve obtained by the method according to the present application.

In yet another aspect, the present application provides the use of a modified Y-type molecular sieve according to the present application in the catalytic cracking of a hydrocarbon feedstock, particularly a hydrogenated light cycle oil, comprising contacting the hydrocarbon feedstock with a catalytic cracking catalyst comprising the modified Y-type molecular sieve under catalytic cracking conditions.

The method for the preparation of a modified Y-type molecular sieve provided in the present application can be used to prepare high-silica Y-type molecular sieve rich in secondary pores with high crystallinity, high thermal stability and high hydrothermal stability by subjecting the Y-type molecular sieve to an ion-exchange with rare earth, a hydrothermal ultra-stabilization treatment and a gas phase ultra-stabilization treatment, in combination with an acid treatment used to clean the pores of the molecular sieve and modifications with the active elements of gallium and in zirconium, as well as phosphorus, so that the degree of ultra-stability of the molecular sieve can be greatly improved while maintaining a high crystallinity thereof. The molecular sieve obtained has a uniform distribution of aluminum, a low non-framework aluminum content, and unobstructed secondary pores.

The modified Y-type molecular sieve according to the present application can be used as an active component of catalytic cracking catalysts for the catalytic cracking of hydrogenated LCOs. When used for processing hydrogenated LCOs, catalytic cracking catalysts prepared by using the molecular sieve as an active component show a high LCO conversion efficiency (such as a high effective conversion rate of LCO), a lower coke selectivity, a higher yield of BTX-rich gasoline, and a high propylene yield.

Other characteristics and advantages of the present application will be described in detail in the detailed description hereinafter.

DETAILED DESCRIPTION OF THE INVENTION

The present application will be further described in detail below with reference to embodiments thereof. It is to be understood that the embodiments described herein are merely illustrative and not restrictive.

Any numerical value (including the end values of numerical ranges) provided herein is not limited to the precise value recited, but should be interpreted as covering any value close to said precise value, such as any possible value within ±5% of said precise value. Moreover, for any numerical range provided herein, one or more new numerical ranges can be obtained by arbitrarily combining the end values of the range, an end value with a specific value provided within the range, or various specific values provided within the range. Such new numerical ranges should also be considered as being specifically disclosed herein.

Unless otherwise indicated, all terms used herein have the same meaning as commonly understood by those skilled in the art, and where the definition of a term provided herein is different from the ordinary understanding in the art, the definition provided herein shall prevail.

In the present application, except for those explicitly stated, any matter or matters not mentioned are directly applicable to those known in the art without any change. Moreover, any of the embodiments described herein can be freely combined with one or more of other embodiments described herein, and the resulting technical solution or technical idea should be considered as a part of the original disclosure or original description of the present application, while should not be considered as a new matter that has not been disclosed or anticipated herein, unless it is apparent to those skilled in the art that such a combination is obviously unreasonable.

The RIPP test methods involved in the present application can be found in "Petrochemical Analysis Methods (RIPP Test Methods)", edited by Cuiding YANG et al., Science Press, September 1990, First Edition, ISBN: 7-03-001894-X, pages 412-415 and 424-426, which is incorporated herein by reference in its entirety.

All patent and non-patent literatures mentioned herein, including but not limited to textbooks and journal articles, are hereby incorporated by reference in their entireties.

As used herein, the terms "Y-type molecular sieve" and "Y-type zeolite" are used interchangeably, and the terms "NaY molecular sieve" and "NaY zeolite" are also used interchangeably.

As used herein, the term "secondary pores" refers to the pores having a pore size (i.e. pore diameter) of from 2 nm to 100 nm in the molecular sieve.

As used herein, the term "inorganic acid having a medium or higher strength" refers to an inorganic acid having an acid strength not lower than that of $HNO_2$ (nitrous acid), including but not limited to $HClO_4$ (perchloric acid), HI (hydrogen iodide), HBr (hydrobromic acid), HCl (hydrochloric acid), $HNO_3$ (nitric acid), $H_2SeO_4$ (selenic acid), $H_2SO_4$ (sulfuric acid), $HClO_3$ (chloric acid), $H_2SO_3$ (sulfuric acid), $H_3PO_4$ (phosphoric acid), and $HNO_2$ (nitrous acid), and the like.

As used herein, the terms "rare earth solution" and "rare earth salt solution" are used interchangeably, and are preferably an aqueous solution of a rare earth salt.

As used herein, the expression "Y-type molecular sieve having a normal lattice constant" means that the lattice constant of the Y-type molecular sieve is within the range of the lattice constant of conventional NaY molecular sieves, which is preferably in a range of about 2.465 nm to about 2.472 nm.

As used herein, the term "atmospheric pressure" means a pressure of about 1 atm.

As used herein, the weight, on a dry basis, of a material refers to the weight of the solid product obtained after calcining the material at 800° C. for 1 hour.

In a first aspect, the present application provides a modified Y-type molecular sieve, having a rare earth content of about 4% to about 11% by weight on the basis of the oxide, a phosphorus content of about 0.05% to about 10% by weight on the basis of $P_2O_5$, a sodium content of no more than about 0.5% by weight on the basis of sodium oxide, a gallium content of about 0.1% to about 2.5% by weight on the basis of gallium oxide, and a zirconium content of about 0.1% to about 2.5% by weight on the basis of zirconia, based on the weight of the modified Y-type molecular sieve on a dry basis; wherein the modified Y-type molecular sieve has a total pore volume of about 0.36 mL/g to about 0.48 mL/g, a percentage of the pore volume of secondary pores having a pore size of 2-100 nm to the total pore volume of about 20% to about 40%; a lattice constant of about 2.440 nm to about 2.455 nm, a lattice collapse temperature of not lower than about 1060° C., a percentage of non-framework aluminum content to the total aluminum content of no more than about 10%, and a ratio of B acid to L acid in the strong acid content of the modified Y-type molecular sieve of no less than about 3.5.

The modified Y-type molecular sieve according to the present application has high degree of ultra-stability, high crystallinity, uniform distribution of aluminum, low non-framework aluminum content, and unobstructed secondary pores. The modified Y-type molecular sieve shows a high LCO conversion efficiency, a lower coke selectivity, a higher yield of BTX-rich gasoline, and a high propylene yield, when used in the processing of hydrogenated LCOs.

The modified Y-type molecular sieve according to the present application comprises rare earth, and the modified Y-type molecular sieve may have a rare earth content of about 4% to about 11% by weight, preferably about 4.5% to about 10% by weight, for example about 5-9% by weight, based on the weight of the modified Y-type molecular sieve on a dry basis.

According to the present application, the kind and composition of the rare earth are not particularly limited. Preferably, the rare earth may comprise La, Ce, Pr or Nd, or a combination of two, three or four of them; optionally, the rare earth may further comprise a rare earth element other than La, Ce, Pr and Nd.

The modified Y-type molecular sieve according to the present application comprises gallium and zirconium as the active elements, and the molecular sieve may have a gallium content calculated on the basis of gallium oxide (also referred to herein as gallium oxide content) of about 0.1-2.5 wt %, preferably about 0.2-2.0 wt % or about 0.3-1.8 wt %, and a zirconium content calculated on the basis of zirconia (also referred to herein as zirconia content) of about 0.1-2.5 wt %, preferably about 0.2-2.0 wt % or about 0.5-2 wt %, based on the weight of the molecular sieve on a dry basis. Within the above preferred ranges, the modified Y-type molecular sieve shows a higher LCO catalytic conversion efficiency, and a lower coke selectivity, and is more favorable for the production of gasoline rich in BTX-aromatics and propylene in a higher yield.

The modified Y-type molecular sieve according to the present application comprises phosphorus as a modifying element to further improve the coke selectivity of the molecular sieve, and the phosphorus content calculated on the basis of $P_2O_5$ (also referred to herein as $P_2O_5$ content) is about 0.05% to about 10% by weight, for example about 0.1-6% by weight, preferably about 1-5.5% by weight, based on the weight of the molecular sieve on a dry basis.

According to the present application, in some embodiments, the modified Y-type molecular sieve may further comprise a small amount of sodium, and the sodium content calculated on the basis of sodium oxide (also referred to herein as sodium oxide content) may be about 0.05-0.5% by weight, for example about 0.1-0.4% by weight, about 0.05-0.3% by weight or about 0.05-0.2% by weight, based on the weight of the molecular sieve on a dry basis.

According to the present application, the contents of rare earth, sodium and the active elements gallium and zirconium in the modified Y-type molecular sieve can be determined by X-ray fluorescence spectrometry, respectively.

According to the present application, the pore structure of the modified Y-type molecular sieve can be further optimized to achieve a more desirable catalytic cracking reaction performance. The total pore volume of the modified Y-type molecular sieve may preferably be about 0.36 mL/g to about 0.48 mL/g, further preferably about 0.38-0.42 or 0.4-0.48 mL/g; a percentage of the pore volume of secondary pores having a pore size of 2-100 nm to the total pore volume may be about 20% to about 40%, preferably about 28-38%, for example about 25-35%. For example, the pore volume of secondary pores having a pore size of 2.0-100 nm may be about 0.08-0.18 mL/g, preferably about 0.10-0.16 mL/g. In the present application, the pore volume of secondary pores can be determined, according to the RIPP 151-90 standard method (see "Petrochemical Analysis Methods (RIPP Test Methods)", Cuiding YANG et al., Science Press, September 1990, pp. 424-426), as follows: determining the total pore volume of the molecular sieve based on the adsorption isotherm, then determining the micropore volume of the molecular sieve based on the adsorption isotherm using the T-plot method, and subtracting the micropore volume from the total pore volume to obtain the pore volume of secondary pores.

The modified Y-type molecular sieve provided in the present application is a rare earth modified ultra-stable Y molecular sieve rich in secondary pores, and the secondary pores of the molecular sieve having a pore size of 2-100 nm show a dual probable pore size distribution, in which the most probable pore size of secondary pores having a relatively smaller pore size is about 2-5 nm, and the most probable pore size of secondary pores having a relatively larger pore size is about 6-20 nm, preferably about 8-18 nm. Preferably, the percentage of the pore volume of secondary pores having a pore size of 2-100 nm to the total pore volume may be about 28-38%, or about 25-35%.

In a preferred embodiment of the present application, the modified Y-type molecular sieve may have a specific surface area of about 600-670 m$^2$/g, for example, about 610-670 m$^2$/g or about 640-670 m$^2$/g or about 646-667 m$^2$/g. The specific surface area of the modified Y-type molecular sieve refers to a BET specific surface area, and can be measured in accordance with the ASTM D4222-98 standard method.

According to the present application, the modified Y-type molecular sieve preferably has a lattice constant of about 2.440 nm to about 2.455 nm, for example, about 2.442-2.453 nm or 2.442-2.451 nm or 2.441-2.453 nm.

According to the present application, the modified Y-type molecular sieve may preferably has a lattice collapse temperature of about 1065° C. to about 1085° C., more preferably about 1065-1083° C.

According to the present application, the modified Y-type molecular sieve may have a relative crystallinity of no less than about 70%, for example, about 70% to about 80%, preferably about 70-76%. The modified Y-type molecular sieve according to the present application has high hydrothermal aging resistance, and the modified Y-type molecular sieve shows a relative crystallinity retention of about 38% or more, for example about 38-60%, or about 50-60%, or about 46-58%, as determined by XRD, after aging at 800° C. under normal pressure in 100% steam atmosphere for 17 h.

According to the present application, the lattice collapse temperature of the modified Y-type molecular sieve can be determined by differential thermal analysis (DTA). The lattice constant and relative crystallinity of the molecular sieve can be determined by X-ray powder diffraction (XRD) according to the RIPP 145-90 and RIPP 146-90 standard methods (see "Petrochemical Analysis Methods (RIPP Test Methods)", Cuiding YANG et al., Science Press, September 1990, pp. 412-415).

According to the present application, the framework silica-alumina ratio of the modified Y-type molecular sieve is calculated according to the following equation:

$$\text{Framework SiO}_2/\text{Al}_2\text{O}_3 \text{ molar ratio} = (2.5858 - a_0) \times 2/(a_0 - 2.4191),$$

wherein $a_0$ refers to the lattice constant of which the unit is nm.

According to the present application, the total silica-alumina ratio of the modified Y-type molecular sieve can be calculated based on the content of Si and Al elements determined by X-ray fluorescence spectrometry; and the percentage of framework Al to the total Al can be calculated based on the framework silica-alumina ratio determined by XRD and the total silica-alumina ratio determined by XRF, and in turn the percentage of non-framework Al to the total Al can be calculated.

According to the present application, the relative crystallinity retention of the modified Y-type molecular sieve = (relative crystallinity of aged sample/relative crystallinity of fresh sample)×100%.

The modified Y-type molecular sieve according to the present application has a low non-framework aluminum content, a percentage of non-framework aluminum content to the total aluminum content of no more than about 10%, further preferably about 5% to about 9.8%, or about 6-9.8%; and a framework silica-alumina ratio, calculated on the basis of $n\text{SiO}_2/n(\text{Al}_2\text{O}_3)$ (i.e. $\text{SiO}_2/\text{Al}_2\text{O}_3$ molar ratio), of about 7 to about 14, preferably about 8.5-12.6 or 9.2-11.4 or 7.6-12.6.

According to the present application, in order to ensure that the modified Y-type molecular sieve has a desirable surface acid center type and strength, the ratio of B acid to L acid in the strong acid content of the modified Y-type molecular sieve is not less than about 3.5, preferably 3.5-6.5, for example, about 3.5-5.8 or 3.5-4.8. The ratio of B acid to L acid in the strong acid content of the modified Y-type molecular sieve, that is, the ratio of the content of strong B acid to the content of strong L acid, can be determined by the pyridine adsorption infrared spectroscopy at 350° C., wherein the strong acid content refers to the total content of strong acid on the surface of the molecular sieve, and the strong acid refers to the acid detected by pyridine adsorption infrared spectroscopy at 350° C.

In a preferred embodiment of the present application, the modified Y-type molecular sieve has a rare earth content of about 4.5-10% by weight on the basis of the oxide, a phosphorus content of about 0.5-5% by weight on the basis of $P_2O_5$, a sodium oxide content of about 0.05-3 wt %, a gallium oxide content of about 0.1-2.5 wt %, such as about 0.2-2 wt %, or about 0.3-1.8 wt %, and a zirconia content of about 0.1-2.5 wt %, such as about 0.5-2.0 wt %, or about 0.2-2 wt %, based on the weight of the modified Y-type molecular sieve on a dry basis; the modified Y-type molecular sieve may have a lattice constant of about 2.442-2.451 nm; and a framework silica-alumina ratio of about 8.5-12.6 calculated on the basis of $n\text{SiO}_2/n(\text{Al}_2\text{O}_3)$.

In a second aspect, the present application provides a method for the preparation of a modified Y-type molecular sieve, comprising the steps of:

(1) contacting a NaY molecular sieve with a rare earth salt solution for ion-exchange reaction, to obtain an ion-exchanged molecular sieve;

(2) subjecting the ion-exchanged molecular sieve to roasting at a temperature of about 350° C. to about 480° C. in an atmosphere comprising about 30 vol % to about 90 vol % of steam for about 4.5 hours to about 7 hours, to obtain a molecular sieve undergone a mild hydrothermal ultra-stabilization treatment;

(3) subjecting the molecular sieve undergone a mild hydrothermal ultra-stabilization treatment to gas phase ultra-stabilization by contacting and reacting with gaseous $SiCl_4$, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification by contacting with a phosphorus compound, to obtain a phosphorus-modified molecular sieve; and (6) subjecting the phosphorus-modified molecular sieve to a modification treatment by contacting with gallium and zirconium in a solution, and then to calcination, to obtain the modified Y-type molecular sieve.

In a particular embodiment, the method according to the present application includes the following steps:

(1) contacting a NaY molecular sieve with a rare earth salt for ion-exchange reaction, filtering and performing a first washing to obtain an ion-exchanged molecular sieve having a sodium oxide content of no more than about 9.5% by weight, based on the weight of the ion-exchanged molecular sieve on a dry basis;

(2) subjecting the ion-exchanged molecular sieve to a first roasting at a temperature of about 350° C. to about 480° C. in an atmosphere comprising about 30 vol % to about 90 vol % of steam for about 4.5 hours to about 7 hours, to obtain a molecular sieve undergone a mild hydrothermal ultra-stabilization treatment;

(3) contacting and reacting the molecular sieve undergone a mild hydrothermal ultra-stabilization treatment with gaseous $SiCl_4$, optionally performing a second washing and a second filtering, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification with a phosphorus compound, to obtain a phosphorus-modified molecular sieve; and (6) subjecting the phosphorus-modified molecular sieve to a modification treatment by contacting with gallium and zirconium in a solution and drying, and then to a second calcination, to obtain the modified Y-type molecular sieve.

The method according to the present application can be used to prepare a high-silica Y-type molecular sieve rich in secondary pores with high crystallinity, high thermal stability and high hydrothermal stability, and can greatly improve the degree of ultra-stability of the molecular sieve while maintaining a high crystallinity. The molecular sieve obtained has a uniform distribution of aluminum, a low non-framework aluminum content, and unobstructed secondary pores. The modified Y-type molecular sieve shows a high LCO conversion efficiency, a lower coke selectivity, a higher yield of gasoline rich in BTX-aromatics, and a high propylene yield, when used in the processing of hydrogenated LCOs.

In the method for the preparation of a modified Y-type molecular sieve provided in the present application, in the step (1), the NaY molecular sieve is subjected to an ion-exchange reaction with a rare earth solution to obtain a rare earth modified Y-type molecular sieve having a normal lattice constant and a reduced sodium oxide content. The ion-exchange reaction can be carried out in accordance with a method well known to those skilled in the art. For example, the ion-exchange reaction may be carried out by: mixing a NaY molecular sieve with water, adding a rare earth salt and/or an aqueous rare earth salt solution under stirring to conduct an ion-exchange reaction, and then filtering and washing.

In a preferred embodiment, in the step (1), the water used may be deionized water; and the NaY molecular sieve may be commercially available or prepared according to existing methods. In an embodiment, the NaY molecular sieve may have a lattice constant of about 2.465 nm to about 2.472 nm, a framework silica-alumina ratio (i.e. $SiO_2/Al_2O_3$ molar ratio) of about 4.5-5.2, and a relative crystallinity of about 85% or more, for example, about 85-95%, and a sodium oxide content of about 13.0-13.8% by weight.

According to the present application, the ion-exchange reaction may be carried out under conditions conventionally used in the art. Preferably, in order to promote the ion-exchange reaction, the ion-exchange reaction of the NaY molecular sieve with the rare earth solution may be carried out at a temperature of about 15° C. to about 95° C., preferably about 65-95° C.; for a period of about 30 min to about 120 min, preferably about 45-90 min; at a weight ratio of the NaY molecular sieve (on a dry basis):rare earth salt (calculated on the basis of $RE_2O_3$):$H_2O$ of about 1:(0.01-0.18):(5-20), preferably about 1:(0.5-0.17):(6-14).

In an embodiment of the present application, the ion-exchange between rare earth ions and sodium ions can be carried out by mixing the NaY molecular sieve and the rare earth salt with water at a weight ratio of NaY molecular sieve:rare earth salt:$H_2O$ of about 1:(0.01-0.18):(5-20), and stirring at about 15-95° C., for example about 65-95° C., preferably for about 30 min to about 120 min. Particularly, the mixing of the NaY molecular sieve, the rare earth salt and water may comprise forming a slurry of the NaY molecular sieve and water, and then adding the rare earth salt and/or an aqueous solution of the rare earth salt to the slurry. The rare earth salt is preferably a rare earth chloride and/or a rare earth nitrate. The rare earth may be any kind of rare earth, and the kind and composition thereof are not particularly limited. For example, the rare earth may be one or more of La, Ce, Pr, Nd, and mixed rare earth. Preferably, the mixed rare earth comprises one or more of La, Ce, Pr, and Nd, or may further comprise at least one of the rare earth elements other than La, Ce, Pr, and Nd.

According to the present application, the washing of the step (1) is intended to wash away the exchanged sodium ions by using deionized water. Preferably, the ion-exchanged molecular sieve obtained in the step (1) may have a rare earth content calculated on the basis of $RE_2O_3$ of about 4.5% to about 13% by weight, for example, about 5.5-13% by weight or 5.5-12% by weight, a sodium oxide content of no more than about 9.5 wt %, for example about 5.5-9.5 wt %, and a lattice constant of about 2.465 nm to about 2.472 nm.

In the method for the preparation of a modified Y-type molecular sieve provided in the present application, in the step (2), the rare earth modified Y-type molecular sieve having a normal lattice constant is roasted at a temperature of about 350° C. to about 480° C. in an atmosphere comprising about 30 vol % to about 90 vol % of steam for about 4.5 hours to about 7 hours. Preferably, the roasting of the step (2) is carried out at a temperature of about 380° C. to about 460° C., in a roasting atmosphere comprising about 40 vol % to about 80 vol % of steam, and for a period of about 5 hours to about 6 hours. Optionally, the steam atmosphere may further comprise other gases, such as one or more of air, helium or nitrogen. Preferably, the molecular sieve obtained in the step (2) undergone a mild hydrothermal ultra-stabilization treatment may have a lattice constant of about 2.450 nm to about 2.462 nm.

According to the present application, the atmosphere comprising 30-90 vol % of steam refers to an atmosphere in which steam is present in an amount of about 30-90% by volume, and the balance is one or more selected from the group consisting of air, helium or nitrogen. For example, an atmosphere comprising 30% by volume of steam may be an atmosphere comprising 30% by volume of steam and 70% by volume of air.

In order to ensure the effect of the gas phase ultra-stabilization treatment, in an embodiment of the present application, the molecular sieve may be dried before the step (3) to reduce the water content in the molecular sieve, so that the molecular sieve to be contacted with $SiCl_4$ in the step (3) has a water content of no more than about 1% by weight. The drying may be, for example, roasting and drying in a rotary roaster or a muffle furnace.

In the method for the preparation of a modified Y-type molecular sieve provided in the present application, the conditions for the contacting and reacting of the step (3) can be varied within a wide range. In order to further enhance the effect of the gas phase ultra-stabilization treatment, preferably, the weight ratio of $SiCl_4$ to the modified molecular sieve undergone a mild hydrothermal ultra-stabilization treatment (on a dry basis) obtained in the step (2) may be about (0.1-0.7):1, preferably about (0.2-0.6):1; the reaction temperature may be about 200° C. to about 650° C., preferably about 350-500° C.; and the reaction time may be about 10 min to about 5 hours, preferably about 0.5-4 h. In the step (3), a second washing and a second filtering may be optionally performed, and drying may be optionally performed after the second filtering. The second washing may be carried out by a conventional washing method, and may be carried out using deionized water. Its purpose is to remove the soluble by-products such as $Na^+$, $Cl^-$ and $Al^{3+}$ remaining in the molecular sieve. The washing may be carried out at the following conditions: a temperature of about 30° C. to about 60° C., a weight ratio of water to the gas phase ultra-stabilized molecular sieve before washing of about (5-20):1, preferably about (6-15):1, and a pH of the spent washing liquid of about 2.5 to about 5.0. Further, the washing can be carried out to an extent that no free ions like $Na^+$, $Cl^-$ and $Al^{3+}$ can be detected in the spent washing liquid.

In the method for the preparation of a modified Y-type molecular sieve provided in the present application, in the step (4), the gas phase ultra-stabilized molecular sieve obtained in the step (3) is contacted and reacted with an acid solution for channel cleaning to make the secondary holes unobstructed, also referred to herein as channel cleaning. In an embodiment of the present application, the contacting and reacting gas phase ultra-stabilized molecular sieve obtained in the step (3) with an acid solution comprising mixing the molecular sieve undergone a gas phase ultra-stabilization treatment with an acid solution, and reacting for a period of time, and then separating the molecular sieve from the acid solution after the reaction, for example, by filtration, and then optionally washing and optionally drying, to obtain the modified Y-type molecular sieve provided in the present application. The gas phase ultra-stabilized molecular sieve may be subjected to an acid treatment by contacting with an acid solution at a temperature of about 60-100° C., preferably about 80-99° C., further preferably about 88-98° C.; for a period of about 1-4 h, preferably about 1-3 h. The acid solution may comprise an organic acid and/or an inorganic acid, and the weight ratio of the acid in the acid solution, water in the acid solution, and the gas phase ultra-stabilized molecular sieve on a dry basis may be about (0.001-0.15):(5-20):1, preferably about (0.002-0.1): (8-15):1 or (0.01-0.05):(8-15):1. Optionally, the step (4) may further comprise washing the acid-treated molecular sieve obtained for the purpose of removing soluble by-products such as $Na^+$, $Cl^+$ and $Al^{3+}$ remaining in the molecular sieve. The washing may be carried out in a same or different way as in the step (3), and may be carried out, for example, under the following conditions: a temperature of about 30° C. to about 60° C., a weight ratio of water to the acid-treated molecular sieve before washing of about (5-20):1, preferably about (6-15):1, and a pH of the spent washing liquid of about 2.5 to about 5.0. Further, the washing can be carried out to an extent that no free ions like $Na^+$, and $Al^{3+}$ can be detected in the spent washing liquid.

In a preferred embodiment, the acid in the acid solution (aqueous acid solution) is at least one organic acid and at least one inorganic acid having a medium or higher strength. The organic acid may comprise oxalic acid, malonic acid, succinic acid, methyl succinic acid, malic acid, tartaric acid, citric acid or salicylic acid, or a combination of two, three or four of them. The inorganic acid having a medium or higher strength may comprise phosphoric acid, hydrochloric acid, nitric acid or sulfuric acid, or a combination of two, three or four of them. The contacting may be carried out at a temperature of preferably about 80° C. to about 99° C., such as about 85-98° C., for a period of about 60 minutes or above, such as about 60 to 240 minutes or 90 to 180 minutes. The weight ratio of the organic acid to the molecular sieve is preferably about (0.02-0.05):1; the weight ratio of the inorganic acid having a medium or higher strength to the molecular sieve is preferably about (0.01-0.06):1, for example, about (0.02)-0.05):1, and the weight ratio of water to the molecular sieve is preferably about (5-20):1, for example about (8-15):1.

In certain preferred embodiments, the acid treatment of step (4), also referred to as channel cleaning, is carried out in two stages, wherein the gas phase ultra-stabilized molecular sieve is subjected to a first contact with an inorganic acid, preferably an inorganic acid having a medium or higher strength, wherein the weight ratio of the inorganic acid having a medium or higher strength to the molecular sieve may be about (0.01-0.05):1, for example, about (0.02-0.05): 1, and the weight ratio of water to the molecular sieve is preferably about (5-20):1, for example, about (8-15):1, the reaction temperature is about 80-99° C., preferably 90-98° C., and the reaction time is about 60 min to about 120 min; and then the resulting molecular sieve is subjected to a second contact with an organic acid, and the weight ratio of the organic acid to the molecular sieve may be about (0.02-0.10):1, for example, about (0.05-0.08):1, and the weight ratio of water to the molecular sieve is preferably about (5-20):1, for example, about (8-15):1, the reaction temperature is about 80-99° C., preferably 90-98° C., and the reaction time is about 60 min to about 120 min, wherein the weight ratio is calculated based on the weight of the molecular sieve on a dry basis.

The method for the preparation of a modified Y-type molecular sieve provided in the present application further comprises subjecting the acid-treated molecular sieve obtained in the step (4) to a phosphorus modification in the step (5). The phosphorus modification may be carried out using a phosphorus compound, for one or more times, to incorporate a desired amount of phosphorus into the molecular sieve, and the phosphorus modification generally comprises contacting the acid-treated molecular sieve with a solution containing a phosphorus compound normally at a temperature of about 15° C. to about 100° C., preferably about 30-95° C., for about 10-100 min, then filtering and washing, wherein the weight ratio of the phosphorus in the solution calculated on the basis of $P_2O_5$, water in the solution, and the molecular sieve is about (0.0005-0.10):(2-5):1, that is, the weight ratio of water in the solution to the molecular sieve is about (2-5):1, preferably about (3-4):1, and the weight ratio of phosphorus (calculated on the basis of $P_2O_5$) to the molecular sieve is about (0.0005-0.10):1, preferably about (0.001-0.06)):1. The phosphorus compound may be one or more selected from the group consisting of phosphoric acid, ammonium phosphate, ammonium dihydrogen phosphate, and diammonium hydrogen phosphate. The washing can be carried out by washing with deionized water in an amount of about 5-15 times the weight of the molecular sieve.

In a preferred embodiment, the phosphorus modification can be carried out by: adding the acid-treated molecular sieve to a solution containing a phosphorus compound, reacting at about 15° C. to about 100° C. for about 10-100 min, filtering and washing; wherein the weight ratio of water in the solution to the molecular sieve is about (2-5):1, preferably about (3-4):1, and the weight ratio of phosphorus (calculated on the basis of $P_2O_5$) to the molecular sieve is about (0.0005-0.10):1, preferably about (0.001-0.06):1.

In the method according to the present application, the phosphorus-modified molecular sieve may be contacted with a solution containing gallium and zirconium in the step (6), and subjected to an exchange and/or immersion treatment, to load the active elements gallium and zirconium onto the modified Y-type molecular sieve. The contact with the active elements gallium and zirconium in the solution may be carried out for one or more times to incorporate the required amount of active elements. In order to enhance the effect of the modification with the gallium element and the zirconium element, in a preferred embodiment of the present application, the molecular sieve may be contacted with a gallium salt and a zirconium salt in the solution, wherein the contact of the molecular sieve with the gallium salt and with the zirconium salt can be conducted simultaneously or in separate stages.

In a preferred embodiment, the molecular sieve can be contacted with the gallium salt and the zirconium salt simultaneously, and the step (6) further comprises: mixing the phosphorus-modified molecular sieve and an aqueous solution containing the gallium salt and the zirconium salt homogeneously and then standing for a period of time. For example, the phosphorus-modified molecular sieve may be added to a solution containing $Ga(NO_3)_3$ and $Zr(NO_3)_4$ under stirring to impregnate it with gallium and zirconium components, stirred homogeneously, and then allowed to stand at about 15° C. to about 40° C. for about 24-36 h. Then, the slurry containing the phosphorus-modified molecular sieve, $Ga(NO_3)_3$ and $Zr(NO_3)_4$ is further stirred for about 20 minutes to obtain a uniform mixture, and then subjected to drying and a second calcination. The drying may be carried out by any drying method, such as flash drying, oven drying, and air drying. In a preferred embodiment, the drying can be carried out by, for example, transferring the slurry to a rotary evaporator and evaporating to dryness while rotating by heating in a water bath. Preferably, the second calcination may comprise placing the dried material in a rotary roaster, and calcining at about 450-600° C. for about 2-5 h, further preferably at about 480-580° C. for about 2.2-4.5 h.

Preferably, the gallium salt may be $Ga(NO_3)_3$, $Ga_2(SO_4)_3$ or $GaCl_3$, or a combination of two or three of them, preferably $Ga(NO_3)_3$; and/or the zirconium salt may be $Zr(NO_3)_4$, $Zr(SO_4)_2$ or $ZrCl_4$, or a combination of two or three of them, preferably $Zr(NO_3)_4$. The weight ratio of gallium in the aqueous solution containing a gallium salt and a zirconium salt calculated on the basis of its oxide, zirconium in the aqueous solution containing a gallium salt and a zirconium salt calculated on the basis of its oxide, and the phosphorus-modified molecular sieve on a dry basis may be about (0.001-0.025):(0.001-0.025):1, preferably about (0.002-0.02):(0.002-0.02):1; and the weight ratio of water in the aqueous solution containing a gallium salt and a zirconium salt to the phosphorus-modified molecular sieve on a dry basis may be about (2-3):1, preferably about (2.2-2.6):1.

In another preferred embodiment, the molecular sieve may be contacted with a gallium salt and a zirconium salt in separate stages. For example, the molecular sieve may be first contacted with an aqueous solution containing a gallium salt, and then contacted with an aqueous solution containing a zirconium salt; or the molecular sieve may be first contacted with an aqueous solution containing a zirconium salt, and then contacted with an aqueous solution containing a gallium salt, and the conditions of the contact, such as the temperature, time, and concentration of gallium and zirconium, may be the same as described above.

In a particular embodiment of the present application, the method for the preparation of a modified Y-type molecular sieve comprises the following steps:

(1) contacting a NaY molecular sieve with a rare earth solution for ion-exchange reaction, filtering and washing to obtain an ion-exchanged molecular sieve, wherein the ion-exchanged molecular sieve has a reduced sodium oxide content, comprises a rare earth element and has a normal lattice constant; the ion-exchange is normally carried out under stirring, at a temperature of about 15° C. to about 95° C., preferably about 65-95° C., for about 30 min to about 120 min;

(2) subjecting the ion-exchanged molecular sieve to roasting at a temperature of about 350-480° C. in an atmosphere comprising about 30-90% by volume of steam for about 4.5-7 hours, and drying, to obtain a molecular sieve undergone a mild hydrothermal ultra-stabilization treatment having a water content of less than about 1% by weight, wherein the lattice constant of the modified molecular sieve undergone a mild hydrothermal ultra-stabilization treatment is reduced to about 2.450 nm to about 2.462 nm;

(3) contacting the modified molecular sieve undergone a mild hydrothermal ultra-stabilization treatment with gaseous $SiCl_4$ vaporized by heat, with the weight ratio of $SiCl_4$:the modified molecular sieve undergone a mild hydrothermal ultra-stabilization treatment (on a dry basis) being about (0.1-0.7):1, reacting at a temperature of about 200° C. to about 650° C. for about 10 min to about 5 h, optionally washing and optionally filtering, to obtain a gas phase ultra-stabilized molecular sieve;

(4) subjecting the gas phase ultra-stabilized molecular sieve to an acid treatment by contacting with an acid solution, wherein the gas phase ultra-stabilized molecular sieve is first mixed with an inorganic acid having a medium or higher strength and water, and reacted at about 80-99° C., preferably about 90-98° C. for at least about 30 min, such as about 60-120 min; then an organic acid is added, reacted at about 80-99° C., preferably about 90-98° C., for at least about 30 min, such as about 60-120 min, filtered, optionally washed and optionally dried, to obtain an acid-treated molecular sieve; wherein preferably, the weight ratio of the organic acid to the gas phase ultra-stabilized molecular sieve on a dry basis is about (0.02-0.10):1, the weight ratio of the inorganic acid having a medium or higher strength to the gas phase ultra-stabilized molecular sieve on a dry basis is about (0.01-0.05):1, and the weight ratio of water to the gas phase ultra-stabilized molecular sieve is about (5-20):1;

(5) adding the acid-treated molecular sieve to a solution containing a phosphorus compound, reacting at a temperature of about 15° C. to about 100° C. for about 10 min to about 100 min, filtering, washing, and optionally drying, to obtain a phosphorus-modified molecular sieve, wherein the weight ratio of water in the solution to the molecular sieve is about 2 to about 5, preferably about 3 to about 4, and the weight ratio of phosphorus (calculated on the basis of $P_2O_5$) to the molecular sieve is about 0.005 to about 0.10, preferably about 0.01 to about 0.05; and (6) adding the phosphorus-modified molecular sieve to a mixed solution containing $Ga(NO_3)_3$ and $Zr(NO_3)_4$ under stirring to impregnate it with gallium and zirconium components, stirring the phosphorus-modified molecular sieve and the mixed solution containing $Ga(NO_3)_3$ and $Zr(NO_3)_4$ homogeneously, then standing at room temperature, with the weight ratio of $Ga(NO_3)_3$ in the mixed solution containing $Ga(NO_3)_3$ and $Zr(NO_3)_4$ calculated on the basis of $Ga_2O_3$ to the phosphorus-modified molecular sieve being about 0.1-2.5:100, the weight ratio of $Zr(NO_3)_4$ in the mixed solution calculated on the basis of $ZrO_2$ to the molecular sieves being about 0.1-2.5:100, the weight ratio of water added to the mixed solution of $Ga(NO_3)_3$ and $Zr(NO_3)_4$ to the phosphorus-modified molecular sieve (on a dry basis) being about (2-3):1, and the impregnation time is about 24 hours, and then, further stirring the mixed slurry containing the modified Y-type molecular sieve, $Ga(NO_3)_3$ and $Zr(NO_3)_4$ for about 20 minutes to obtain a uniform mixture, transferring the mixture to a rotary evaporator and evaporated to dryness while rotating by heating slowly and uniformly, and then placing the dried material in a muffle furnace and calcining at about 450-600° C. for about 2-5 hours, to obtain the modified Y-type molecular sieve according to the present application.

In a third aspect, the present application provides a catalytic cracking catalyst, comprising about 10% to about 50% by weight of a modified Y-type molecular sieve, about 10% to about 40% by weight of an alumina binder calculated on the basis of alumina, and about 10% to about 80% by weight on a dry basis of clay, based on the weight of the catalyst on a dry basis, wherein the modified Y-type molecular sieve is a modified Y-type molecular sieve according to the present application or a modified Y-type molecular sieve obtained by the method according to the present application.

The catalytic cracking catalyst according to the present application shows a high LCO conversion efficiency, a lower coke selectivity, a higher yield of BTX-rich gasoline, and a high propylene yield, when used in the processing of hydrogenated LCOs.

The catalytic cracking catalyst provided in the present application may further comprise an additional molecular sieve other than the modified Y-type molecular sieve, and the additional molecular sieve may be present in an amount of about 0-40% by weight based on the weight of the catalytic cracking catalyst, for example, about 0-30% by weight, or about 1-20% by weight. The additional molecular sieve may be selected from molecular sieves commonly used in catalytic cracking catalysts, such as molecular sieves selected from the group consisting of zeolites having MFI structure, Beta zeolites, other Y-type zeolites or non-zeolitic molecular sieves, or a combination of two, three or four of them.

Preferably, the additional Y-type molecular sieve is present in an amount, on a dry basis, of no more than about 40% by weight, for example, about 0-40% by weight or about 1-20% by weight. The additional Y-type molecular sieve may be, for example, REY, REHY, DASY, SOY, or PSRY, or a combination of two, three or four of them; the zeolite having MFI structure may be, for example, HZSM-5, ZRP, or ZSP, or a combination of two, three or four of them; the beta zeolite may be, for example, Hβ; and the non-zeolitic molecular sieve may be, for example, aluminum phosphate molecular sieves (AlPO molecular sieves) and/or silicoaluminophosphate molecular sieves (SAPO molecular sieves).

In the catalytic cracking catalyst provided in the present application, the modified Y-type molecular sieve is present in an amount on a dry basis of about 10-50% by weight, preferably about 15-45% by weight, for example about 25-40% by weight.

In the catalytic cracking catalyst provided in the present application, the clay may be one or more selected from the group consisting of clays suitable for use as a component in cracking catalysts, such as selected from the group consisting of kaolin, hydrated halloysite, montmorillonite, diatomaceous earth, halloysite, saponite, rector, sepiolite, attapulgite, hydrotalcite, or bentonite, or a combination of two, three or four of them. These clays are well known to those of ordinary skill in the art. Preferably, the clay is present in the catalytic cracking catalyst according to the present application in an amount of about 20-55% by weight, or about 30-50% by weight on a dry basis.

In the catalytic cracking catalyst provided in the present application, the alumina binder is present in an amount of about 10-40% by weight, for example, about 20-35% by weight, calculated on the basis of alumina. The alumina binder may be one or more selected from the group consisting of the various forms of alumina, hydrated alumina, and aluminum sol typically used in cracking catalysts. For example, it can be selected from the group consisting of γ-alumina, η-alumina, θ-alumina, χ-alumina, pseudo-boemite, boehmite, gibbsite, bayerite or aluminum sol, or a combination of two, three or four thereof, preferably pseudo-boehmite and aluminum sol. For example, the catalytic cracking catalyst may comprise about 2-15% by weight, preferably about 3-10% by weight, of an aluminium sol calculated on the basis of alumina, and about 10-30% by weight, preferably about 15-25% by weight, of pseudo-boehmite calculated on the basis of alumina.

In a fourth aspect, the present application provides a method for the preparation of a catalytic cracking catalyst, comprising the steps of: providing a modified Y-type molecular sieve, forming a slurry comprising the modified Y-type molecular sieve, an alumina binder, clay, and water, spray drying, optionally washing and optionally drying, to obtain the catalytic cracking catalyst, wherein said providing a modified Y-type molecular sieve comprises providing a modified Y-type molecular sieve according to the present application, or preparing a modified Y-type molecular sieve by the method according to the present application.

Except for the step of providing a modified Y-type molecular sieve, all of the steps of the method for the preparation of a catalyst according to the present application can be carried out according to the existing methods, for example, according to the methods described in Chinese Patent Application Publication Nos. CN1098130A and CN1362472A.

In the method for the preparation of a catalyst provided in the present application, the spray drying, washing and drying can be carried out according to the methods known in the prior art, and there is no special requirements in the present application.

In the method for the preparation of a catalyst provided in the present application, the modified Y-type molecular sieve may be used in any amount conventionally used in the art. Preferably, the modified Y-type molecular sieve may be present in the catalyst obtained in an amount on a dry basis of about 10-50% by weight, preferably about 15-45% by weight, for example about 25-40% by weight.

In the method for the preparation of a catalyst provided in the present application, the clay may be one or more selected from the group consisting of clays suitable for use as a component in cracking catalysts, such as one or more selected form the group consisting of kaolin, hydrated halloysite, montmorillonite, diatomaceous earth, halloysite, saponite, rector, sepiolite, attapulgite, hydrotalcite, and bentonite. These clays are well known to those of ordinary skill in the art. The clay may be used in any amount conventionally used in the art. Preferably, the clay is present in the catalytic cracking catalyst obtained in an amount of about 20-55% by weight, or about 30-50% by weight on a dry basis.

In the method for the preparation of a catalyst provided in the present application, the alumina binder may be one or more selected from the group consisting of the various forms of alumina, hydrated alumina, and aluminum sol typically used in cracking catalysts. For example, it can be one or more selected from the group consisting of γ-alumina, η-alumina, θ-alumina, χ-alumina, pseudoboemite, boehmite, gibbsite, bayerite or aluminum sol, preferably pseudoboehmite and aluminum sol. The alumina binder may be used in any amount conventionally used in the art. Preferably, the alumina binder is present in the catalytic cracking catalyst obtained in an amount calculated on the basis of alumina of about 10-40% by weight, for example about 20-35% by weight. In an embodiment, the alumina binder is pseudo-boehmite and aluminium sol, and the catalytic cracking catalyst obtained may comprise about 2-15% by weight, preferably about 3-10% by weight, of an aluminium sol calculated on the basis of alumina, and about 10-30% by weight, preferably about 15-25% by weight, of pseudo-boehmite calculated on the basis of alumina.

In a fifth aspect, the present application provides the use of a modified Y-type molecular sieve according to the present application in the catalytic cracking of a hydrocarbon feedstock, particularly a hydrogenated light cycle oil, comprising contacting the hydrocarbon feedstock with a catalytic cracking catalyst comprising the modified Y-type molecular sieve under catalytic cracking conditions.

In a sixth aspect, the present application provides the use of a catalytic cracking catalyst according to the present application in the catalytic cracking of a hydrocarbon feedstock, particularly a hydrogenated light cycle oil, comprising contacting the hydrocarbon feedstock with the catalytic cracking catalyst under catalytic cracking conditions.

In a seventh aspect, the present application provides a catalytic cracking process for processing a hydrogenated light cycle oil (hydrogenated LCO) comprising a step of contacting, under catalytic cracking conditions, the hydrogenated LCO with a catalytic cracking catalyst according to the present application or a catalytic cracking catalyst comprising a modified Y-type molecular sieve according to the present application.

According to the present application, preferably, the catalytic cracking conditions may include: a reaction temperature of about 500° C. to about 610° C., a weight hourly space velocity of about 2 $h^{-1}$ to about 16 $h^{-1}$, and a catalyst-to-oil weight ratio of about 3 to about 10.

According to the present application, preferably, the hydrogenated LCO may have the following properties: a density (at 20° C.) of about 0.850-0.920 g/cm$^3$, an H content of about 10.5-12 wt %, an S content of <50 μg/g, and an N content of <10 μg/g, a total aromatics content of about 70-85 wt %, and a polycyclic aromatics content of <15 wt %.

In certain preferred embodiments, the present application provides the following technical solutions:

A1. A modified Y-type molecular sieve, characterized in that, the modified Y-type molecular sieve has a rare earth content of about 4-11% by weight, a phosphorus content calculated on the basis of $P_2O_5$ of about 0.05% to about 10% by weight, a sodium oxide content of no more than about 0.5% by weight, a gallium oxide content of about 0.1% to about 2.5% by weight, and a zirconia content of about 0.1% to about 2.5% by weight, based on the weight of the modified Y-type molecular sieve on a dry basis; the modified Y-type molecular sieve has a total pore volume of about 0.36 mL/g to about 0.48 mL/g, a percentage of the pore volume of secondary pores having a pore size of 2-100 nm to the total pore volume of about 20% to about 40%; a lattice constant of about 2.440 nm to about 2.455 nm and a lattice collapse temperature of not lower than about 1060° C.; a percentage of non-framework aluminum content to the total aluminum content of the modified Y-type molecular sieve of no more than about 10%, and a ratio of B acid to L acid in the strong acid content of the modified Y-type molecular sieve of not less than about 3.5.

A2. The modified Y-type molecular sieve according to Item A1, wherein the percentage of the pore volume of secondary pores having a pore size of 2-100 nm of the modified Y-type molecular sieve to the total pore volume is about 28-38%.

A3. The modified Y-type molecular sieve according to Item A1, wherein the modified Y-type molecular sieve has a ratio of non-framework aluminum content to the total aluminum content of about 5% to about 9.5%; and a framework silica-alumina ratio of about 7 to about 14 calculated on the basis of $nSiO_2/n(Al_2O_3)$.

A4. The modified Y-type molecular sieve according to Item A1, wherein the modified Y-type molecular sieve has a lattice collapse temperature of about 1065° C. to about 1085° C.

A5. The modified Y-type molecular sieve according to Item A1, wherein the ratio of B acid to L acid in the strong acid content of the modified Y-type molecular sieve is about 3.5 to about 6.5, as determined by pyridine adsorption infrared spectroscopy at 350° C.

A6. The modified Y-type molecular sieve according to Item A1, wherein the modified Y-type molecular sieve has a relative crystallinity of about 70% to about 80%.

A7. The modified Y-type molecular sieve according to Item A1, wherein the modified Y-type molecular sieve shows a relative crystallinity retention of about 38% or more as determined by XRD after aging at 800° C. in a 100% steam atmosphere for 17 h.

A8. The modified Y-type molecular sieve according to any one of Items A1 to A7, wherein the modified Y-type molecular sieve has a rare earth content of about 4.5% to about 10% by weight on the basis of the oxide, a phosphorus content of about 0.5% to about 5% by weight on the basis of $P_2O_5$, a sodium oxide content of about 0.05% to about 0.3% by weight, a gallium oxide content of about 0.2% to about 2% by weight, and a zirconia content of about 0.5% to about 2% by weight, based on the weight of the modified Y-type molecular sieve on a dry basis; and the modified Y-type molecular sieve has a lattice constant of about 2.442-2.451 nm, and a framework silica-alumina ratio of about 8.5 to about 12.6, calculated on the basis of $nSiO_2/n(Al_2O_3)$;

wherein the rare earth comprises La, Ce, Pr or Nd, or a combination of two, three, or four of them.

A9. A method for the preparation of a modified Y-type molecular sieve according to any one of Items A1 to A8, characterized in that, the method comprises the steps of:

(1) contacting a NaY molecular sieve with a rare earth salt for ion-exchange reaction, filtering and performing a first washing, to obtain an ion-exchanged molecular sieve, wherein the ion-exchanged molecular sieve has a sodium oxide content of no more than about 9.0% by weight, based on the weight of the ion-exchanged molecular sieve on a dry basis;

(2) subjecting the ion-exchanged molecular sieve to a first roasting at a temperature of about 350° C. to about 480° C. in an atmosphere comprising about 30 vol % to about 90 vol % of steam for about 4.5 hours to about 7 hours, to obtain a molecular sieve undergone a mild hydrothermal ultra-stabilization treatment;

(3) contacting and reacting the molecular sieve undergone a mild hydrothermal ultra-stabilization treatment with $SiCl_4$, optionally performing a second washing and a second filtering, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification with a phosphorus compound, to obtain a phosphorus-modified molecular sieve; and (6) contacting the phosphorus-modified molecular sieve with gallium and zirconium in a solution, and subjecting the resultant to drying and a second calcination, to obtain the modified Y-type molecular sieve.

A10. The method according to Item A9, wherein the ion-exchange is carried out by: mixing a NaY molecular sieve with water, adding a rare earth salt and/or an aqueous rare earth salt solution under stirring to conduct an ion-exchange reaction, filtering and washing;

wherein the ion-exchange is carried out under the following conditions: a temperature of about 15° C. to about 95° C., a period of about 30 min to about 120 min, and a weight ratio of the NaY molecular sieve, rare earth salt and water of about 1:(0.01-0.18):(5-20).

A11. The method according to Item A9 or A10, wherein the ion-exchanged molecular sieve has a lattice constant of about 2.465 nm to about 2.472 nm, a rare earth content of about 4.5% to about 13% by weight on the basis of the oxide, and a sodium oxide content of about 4.5-9.5% by weight.

A12. The method according to Item A9 or A10, wherein the rare earth salt is rare earth chloride or rare earth nitrate.

A13. The method according to Item A9, wherein the step (2) is carried out by: performing a first roasting at a temperature of about 380° C. to about 460° C. in an atmosphere comprising about 40 vol % to about 80 vol % of steam for about 5 hours to about 6 hours.

A14. The method according to Item A9 or A13, wherein the modified molecular sieve undergone a mild hydrothermal ultra-stabilization treatment has a lattice constant of about 2.450 nm to about 2.462 nm, and a water content of no more than about 1% by weight.

A15. The method according to Item A9, wherein, in the step (3), the weight ratio of $SiCl_4$ to the modified molecular sieve undergone a mild hydrothermal ultra-stabilization treatment on a dry basis is about (0.1-0.7):1, the reaction temperature is about 200° C. to about 650° C., and the reaction time is about 10 min to about 5 hours; and the second washing comprises washing to an extent that no free ions like $Na^+$, $Cl^-$ and $Al^{3+}$ can be detected in the spent washing liquid, and the washing conditions may include: a temperature of about 30° C. to about 60° C., a weight ratio of water to the gas phase ultra-stabilized molecular sieve before washing of about (6-15):1, and a pH of the spent washing liquid of about 2.5 to about 5.0.

A16. The method according to Item A9, wherein the acid treatment of the step (4) is carried out under the following conditions: an acid treatment temperature of about 80-99° C., an acid treatment time of about 1-4 h, an acid solution comprising an organic acid and/or an inorganic acid, and a weight ratio of the acid in the acid solution, water in the acid solution and the gas phase ultra-stabilized molecular sieve on a dry basis of about (0.001-0.15):(5-20):1.

A17. The method according to Item A9, wherein the acid treatment of the step (4) is carried out by: subjecting the gas phase ultra-stabilized molecular sieve to a first contact with an inorganic acid solution, and then to a second contact with an organic acid solution, wherein the first contact is conducted under the following conditions: a contact time of about 60 min to about 120 min, a contact temperature of about 90° C. to about 98° C., and a weight ratio of the inorganic acid in the inorganic acid solution, water in the inorganic acid solution, and the gas phase ultra-stabilized molecular sieve on a dry basis of about (0.01-0.05):(5-20):1; and the second contact is conducted under the following conditions: a contact time of about 60 min to about 120 min, a contact temperature of about 90° C. to about 98° C., and a weight ratio of the organic acid in the organic acid solution, water in the organic acid solution, and the gas phase ultra-stabilized molecular sieve on a dry basis of about (0.02-0.1):(5-20):1.

A18. The method according to Item A16 or A17, wherein the organic acid is oxalic acid, malonic acid, succinic acid, methyl succinic acid, malic acid, tartaric acid, citric acid or salicylic acid, or a combination of two, three or four of them; and the inorganic acid is phosphoric acid, hydrochloric acid, nitric acid or sulfuric acid, or a combination of two, three or four of them.

A19. The method according to Item A9, wherein the phosphorus compound is phosphoric acid, ammonium phosphate, ammonium dihydrogen phosphate or diammonium hydrogen phosphate, or a combination of two, three or four of them; the phosphorus modification comprises: contacting the acid-treated molecular sieve with a solution containing a phosphorus compound, reacting at a temperature of about 15° C. to about 100° C. for about 10 min to about 100 min, filtering and washing, wherein the weight ratio of the phosphorus in the solution calculated on the basis of $P_2O_5$, water in the solution, and the acid-treated molecular sieve is about (0.0005-0.10):(2-5):1.

A20. The method according to Item A9, wherein the contacting of the step (6) further comprises: mixing the phosphorus-modified molecular sieve with an aqueous solution containing a gallium salt and a zirconium salt, and then standing at about 15° C. to about 40° C. for about 24 hours to about 36 hours, wherein the weight ratio of gallium in the aqueous solution containing the gallium salt and the zirconium salt calculated on the basis of its oxide, zirconium in the aqueous solution containing the gallium salt and the zirconium salt calculated on the basis of its oxide, and the phosphorus-modified molecular sieve on a dry basis is about (0.001-0.025):(0.001-0.025):1, and the weight ratio of water in the aqueous solution to the phosphorus-modified molecular sieve on a dry basis is about (2-3):1.

A21. The method according to Item A9, wherein, in the step (6), the second calcination is carried out under the following conditions: a calcination temperature of about 450-600° C., and a calcination time of about 2-5 h.

B1. A catalytic cracking catalyst, characterized in that, the catalyst comprises about 10-50% by weight of a modified Y-type molecular sieve, about 10-40% by weight of an alumina binder calculated on the basis of alumina, and about 10-80% by weight on a dry basis of clay, based on the weight of the catalyst on a dry basis;

wherein the modified Y-type molecular sieve has a rare earth content of about 4% to about 11% by weight on the basis of the oxide, a phosphorus content of about 0.05% to about 10% by weight on the basis of $P_2O_5$, a sodium oxide content of no more than about 0.5% by weight, a gallium oxide content of about 0.1% to about 2.5% by weight, and a zirconia content of about 0.1% to about 2.5% by weight, based on the weight of the modified Y-type molecular sieve on a dry basis; and the modified Y-type molecular sieve has a total pore volume of about 0.36 mL/g to about 0.48 mL/g, a percentage of the pore volume of secondary pores having a pore size of 2-100 nm to the total pore volume of about 20% to about 40%; a lattice constant of about 2.440 nm to about 2.455 nm; a lattice collapse temperature of not lower than about 1060° C.; a ratio of non-framework aluminum content to the total aluminum content of the modified Y-type molecular sieve of no more than about 10%, and a ratio of B acid to L acid in the strong acid content of the modified Y-type molecular sieve of no less than about 3.5.

B2. The catalytic cracking catalyst according to Item B1, wherein the modified Y-type molecular sieve has a percentage of the pore volume of secondary pores having a pore size of 2-100 nm to the total pore volume of about 28-38%.

B3. The catalytic cracking catalyst according to Item B1, wherein the modified Y-type molecular sieve has a ratio of non-framework aluminum content to the total aluminum content of about 5% to about 9.5%; and a framework silica-alumina ratio of about 7 to about 14 calculated on the basis of $nSiO_2/n(Al_2O_3)$.

B4. The catalytic cracking catalyst according to Item B1, wherein the modified Y-type molecular sieve has a lattice collapse temperature of about 1065° C. to about 1085° C.

B5. The catalytic cracking catalyst according to Item B1, wherein the ratio of B acid to L acid in the strong acid content of the modified Y-type molecular sieve is about 3.5-6.5, as determined by pyridine adsorption infrared spectroscopy at 350° C.

B6. The catalytic cracking catalyst according to Item B1, wherein the modified Y-type molecular sieve has a relative crystallinity of about 70% to about 80%.

B7. The catalytic cracking catalyst according to Item B1, wherein the modified Y-type molecular sieve shows a relative crystallinity retention of about 38% or more as determined by XRD, after aging at 800° C. in a 100% steam atmosphere for 17 h.

B8. The catalytic cracking catalyst according to any one of Items B1 to B7, wherein the modified Y-type molecular sieve has a rare earth content of about 4.5-10% by weight on the basis of the oxide, a phosphorus content of about 0.5-5% by weight on the basis of $P_2O_5$, a sodium oxide content of about 0.05-0.3% by weight, a gallium oxide content of about 0.2% to about 2% by weight, and a zirconia content of about 0.5% to about 2% by weight, based on the weight of the modified Y-type molecular sieve on a dry basis; and the modified Y-type molecular sieve has a lattice constant of about 2.442-2.451 nm; and a framework silica-alumina ratio of about 8.5 to about 12.6, calculated on the basis of $nSiO_2/n(Al_2O_3)$;

wherein the rare earth comprises La, Ce, Pr or Nd, or a combination of two, three or four of them.

B9. The catalytic cracking catalyst according to Item B1, wherein the clay is kaolin, hydrated halloysite, montmorillonite, diatomaceous earth, halloysite, saponite, rectorite, sepiolite, attapulgite, hydrotalcite or bentonite, or a combination of two, three or four of them; and the alumina binder is alumina, hydrated alumina or aluminum sol, or a combination of two, three or four of them.

B10. A method for the preparation of a catalytic cracking catalyst according to any one of Items B1 to B9, characterized in that, the method comprises: preparing a modified Y-type molecular sieve, forming a slurry comprising the modified Y-type molecular sieve, an alumina binder, clay and water, and spray drying to obtain the catalytic cracking catalyst;

wherein said preparing a modified Y-type molecular sieve comprises the following steps:

(1) contacting a NaY molecular sieve with a rare earth salt for ion-exchange reaction, filtering and performing a first washing, to obtain an ion-exchanged molecular sieve, wherein the ion-exchanged molecular sieve has a sodium oxide content of no more than about 9.0% by weight, based on the weight of the ion-exchanged molecular sieve on a dry basis;

(2) subjecting the ion-exchanged molecular sieve to a first roasting at a temperature of about 350° C. to about 480° C. in an atmosphere comprising about 30 vol % to about 90 vol % of steam for about 4.5 hours to about 7 hours, to obtain a molecular sieve undergone a mild hydrothermal ultra-stabilization treatment;

(3) contacting and reacting the molecular sieve undergone a mild hydrothermal ultra-stabilization treatment with $SiCl_4$, optionally performing a second washing and a second filtering, to obtain a gas phase ultra-stabilized molecular sieve;

(4) subjecting the gas phase ultra-stabilized molecular sieve to an acid treatment by contacting with an acid solution, to obtain an acid-treated molecular sieve;

(5) subjecting the acid-treated molecular sieve to phosphorus modification with a phosphorus compound, to obtain a phosphorus-modified molecular sieve; and (6) contacting the phosphorus-modified molecular sieve with gallium and zirconium in a solution, and subjecting the resultant to drying and a second calcination, to obtain the modified Y-type molecular sieve.

B11. The method according to Item B10, wherein the ion-exchange is carried out by: mixing the NaY molecular sieve with water, adding a rare earth salt and/or an aqueous rare earth salt solution under stirring to conduct an ion-exchange reaction, filtering and washing;

wherein the ion-exchange is carried out under the following conditions: a temperature of about 15° C. to about 95° C., a period of about 30 min to about 120 min, and a weight ratio of the NaY molecular sieve, rare earth salt and water of about 1:(0.01-0.18):(5-20).

B12. The method according to Item B10 or B11, wherein the ion-exchanged molecular sieve has a lattice constant of about 2.465 nm to about 2.472 nm, a rare earth content of about 4.5% to about 13% by weight on the basis of the oxide, and a sodium oxide content of about 4.5-9.5% by weight.

B13. The method according to Item B10 or B11, wherein the rare earth salt is rare earth chloride or rare earth nitrate.

B14. The method according to Item B10, wherein the step (2) is carried out by: performing the first roasting at a temperature of about 380° C. to about 460° C. in an atmosphere comprising about 40 vol % to about 80 vol % of steam for about 5 hours to about 6 hours.

B15. The method according to Item B10 or B14, wherein the modified molecular sieve undergone a mild hydrothermal ultra-stabilization treatment has a lattice constant of about 2.450 nm to about 2.462 nm, and a water content of no more than about 1% by weight.

B16. The method according to Item B10, wherein, in the step (3), the weight ratio of $SiCl_4$ to the modified molecular sieve undergone a mild hydrothermal ultra-stabilization treatment on a dry basis is about (0.1-0.7):1, the reaction temperature is about 200° C. to about 650° C., and the reaction time is about 10 min to about 5 hours; and the second washing comprises washing to an extent that no free ions like $Na^+$, $Cl^-$ and $Al^{3+}$ can be detected in the spent washing liquid, and the washing conditions may include: a temperature of about 30° C. to about 60° C., a weight ratio of water to the gas phase ultra-stabilized molecular sieve before washing of about (6-15):1, and a pH of the spent washing liquid of about 2.5 to about 5.0.

B17. The method according to Item B10, wherein the acid treatment of the step (4) is carried out under the following conditions: an acid treatment temperature of about 80-99° C., an acid treatment time of about 1-4 h, an acid solution comprising an organic acid and/or an inorganic acid, and a weight ratio of the acid in the acid solution, water in the acid solution and the gas phase ultra-stabilized molecular sieve on a dry basis of about (0.001-0.15):(5-20):1.

B18. The method according to Item B10, wherein the acid treatment of the step (4) is carried out by: subjecting the gas phase ultra-stabilized molecular sieve to a first contact with an inorganic acid solution, and then to a second contact with an organic acid solution, wherein the first contact is conducted under the following conditions: a contact time of about 60 min to about 120 min, a contact temperature of about 90° C. to about 98° C., and a weight ratio of the inorganic acid in the inorganic acid solution, water in the inorganic acid solution, and the gas phase ultra-stabilized molecular sieve on a dry basis of about (0.01-0.05):(5-20):1; and the second contact is conducted under the following conditions: a contact time of about 60 min to about 120 min, a contact temperature of about 90° C. to about 98° C., and a weight ratio of the organic acid in the organic acid solution, water in the organic acid solution, and the gas phase ultra-stabilized molecular sieve on a dry basis of about (0.02-0.1):(5-20):1.

B19. The method according to Item B17 or B18, wherein the organic acid is oxalic acid, malonic acid, succinic acid, methyl succinic acid, malic acid, tartaric acid, citric acid or salicylic acid, or a combination of two, three or four of them; and the inorganic acid is phosphoric acid, hydrochloric acid, nitric acid or sulfuric acid, or a combination of two, three or four of them.

B20. The method according to Item B10, wherein the phosphorus compound is phosphoric acid, ammonium phosphate, ammonium dihydrogen phosphate or diammonium hydrogen phosphate, or a combination of two, three or four of them; the phosphorus modification comprises: contacting the acid-treated molecular sieve with a solution containing a phosphorus compound, reacting at a temperature of about 15° C. to about 100° C. for about 10 min to about 100 min, filtering and washing, wherein the weight ratio of the phosphorus in the solution calculated on the basis of $P_2O_5$, water in the solution, and the acid-treated molecular sieve is about (0.0005-0.10):(2-5):1.

B21. The method according to Item B10, wherein the contacting of the step (6) further comprises: mixing the phosphorus-modified molecular sieve with an aqueous solution containing a gallium salt and a zirconium salt, and then standing at about 15° C. to about 40° C. for about 24 hours to about 36 hours, wherein the weight ratio of gallium in the aqueous solution containing the gallium salt and the zirconium salt calculated on the basis of its oxide, zirconium in the aqueous solution containing the gallium salt and the zirconium salt calculated on the basis of its oxide, and the phosphorus-modified molecular sieve on a dry basis is about (0.001-0.025):(0.001-0.025):1, and the weight ratio of water in the aqueous solution to the phosphorus-modified molecular sieve on a dry basis is about (2-3):1.

B22. The method according to Item B10, wherein, in the step (6), the second calcination is carried out under the following conditions: a calcination temperature of about 450-600° C., and a calcination time of about 2-5 h.

B23. Use of the catalytic cracking catalyst according to any one of Items B1 to B9 in the catalytic cracking of a hydrocarbon feedstock.

B24. A catalytic cracking process for processing a hydrogenated LCO, comprising a step of contacting the hydrogenated LCO with a catalyst according to any one of Items B1 to B9 under catalytic cracking conditions; wherein the catalytic cracking conditions include: a reaction temperature of about 500° C. to about 610° C., a weight hourly space velocity of about 2 $h^{-1}$ to about 16 $h^{-1}$, and a catalyst-to-oil weight ratio of about 3 to about 10.

EXAMPLES

The present application will be further illustrated by the following examples, without however limiting the present invention.

In the following examples and comparative examples, NaY molecular sieves (also referred to as NaY zeolites) are supplied by Qilu Branch of Sinopec Catalyst Co., Ltd., of which the sodium oxide content is 13.5% by weight, the framework silica-alumina ratio ($SiO_2/Al_2O_3$ molar ratio) is 4.6, the lattice constant is 2.470 nm, and the relative crystallinity is 90%; rare earth chloride, rare earth nitrate, gallium nitrate and zirconium nitrate are chemically pure reagents produced by Beijing Chemical Plant; pseudo-boehmite is an industrial product produced by Shandong Aluminum Plant with a solid content of 61% by weight; kaolin is a kaolin specialized for cracking catalysts produced by China Kaolin Clay Co., Ltd. of Suzhou with a solid content of 76% by weight; aluminum sol is supplied by Qilu Branch of Sinopec Catalyst Co., Ltd. having an alumina content of 21% by weight.

Unless otherwise stated, the reagents used in each of the comparative examples and examples were commercially available, chemically pure reagents.

Analytical Method:

In each of the comparative examples and examples, the element content of the molecular sieve was determined by X-ray fluorescence spectrometry; the lattice constant and relative crystallinity of the molecular sieve were determined by X-ray powder diffraction (XRD) according to the RIPP 145-90, RIPP 146-90 standard method (see "Petrochemical Analysis Methods (RIPP Test Methods)", edited by Cuiding YANG et al., Science Press, September 1990, pp. 412-415).

The framework silica-alumina ratio of the molecular sieve was calculated according to the following equation:

$$\text{Framework } SiO_2/Al_2O_3 \text{ molar ratio} = (2.5858-a_0) \times 2/(a_0-2.4191),$$

wherein $a_0$ refers to the lattice constant of which the unit is nm.

The total silica-alumina ratio of the molecular sieve was calculated based on the content of Si and Al elements determined by X-ray fluorescence spectrometry. The percentage of the framework Al content to the total Al content was calculated based on the framework silica-alumina ratio determined by XRD and the total silica-alumina ratio determined by XRF, and then the percentage of non-framework Al content to the total Al content was calculated.

The lattice collapse temperature was determined by differential thermal analysis (DTA).

In each of the comparative examples and examples, the acid center type of the molecular sieve and the acid content thereof were determined by pyridine adsorption infrared spectroscopy. The instrument was IFS113V type FT-IR (Fourier transform infrared) spectrometer of Bruker Company, USA. The method for determining the acid content by pyridine adsorption infrared spectroscopy at 350° C. was as follows: a self-supported sample tablet was placed in an in-situ cell of an infrared spectrometer and sealed; the sample was heated to a temperature of 400° C., vacuumed to $10^{-3}$ Pa, and maintained at the temperature for 2 h to remove the gas molecules adsorbed by the sample; the sample was cooled to room temperature, a pyridine vapor at a pressure of 2.67 Pa was introduced, and the sample was maintained under such conditions for 30 min to achieve an adsorption equilibrium; then the sample was heated to a temperature of 350° C., and vacuumed to $10^{-3}$ Pa for desorption for 30 min; after that, the sample was cooled to room temperature and subjected to spectrographic analysis at a scanning wave number range of 1400 $cm^{-1}$ to 1700 $cm^{-1}$, and the pyridine adsorption infrared spectrum of the sample desorbed at 350° C. was obtained. The relative amount of strong Brönsted acid center (B acid center) and strong Lewis acid center (L acid center) in the molecular sieve was obtained based on the intensity of the characteristic adsorption peaks at 1540 $cm^{-1}$ and 1450 $cm^{-1}$ in the pyridine adsorption infrared spectrum.

In each of the comparative examples and examples, the method for determining the pore volume of secondary pores was as follows: according to the RIPP 151-90 standard method (see "Petrochemical Analysis Methods (RIPP Test Methods)", Cuiding YANG et al., Science Press, September 1990, pp. 424-426), the total pore volume of the molecular sieve was determined based on the adsorption isotherm, and then the micropore volume of the molecular sieve was determined based on the adsorption isotherm according to the T-plot method, and the pore volume of secondary pores was obtained by subtracting the micropore volume from the total pore volume.

The following Examples 1-4 are directed to the preparation of the modified Y-type molecular sieve and the catalytic cracking catalyst according to the present application.

Example 1

2000 kg (weight on a dry basis) NaY zeolite having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 $m^3$ of water and stirred evenly at 25° C. Then, 600 L of $RECl_3$ solution (the rare earth concentration calculated on the basis of $RE_2O_3$ in the $RECl_3$ solution being 319 g/L) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y zeolite was 0.5:1, the feed rate of the molecular sieve was 800 kg/h, and the reaction temperature was 400° C. The molecular sieve material obtained after the gas phase ultra-stabilization was separated by a gas-solid separator, sent to a secondary exchange tank containing 20 $m^3$ of water added in advance, and stirred evenly. The weight of the molecular sieve material added to the secondary exchange tank was 2000 kg (weight on a dry basis). Thereafter, 0.6 $m^3$ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.04, and the weight ratio of water to the molecular sieve was 2.5, and the reaction was conducted at 50° C. for 60 min, followed by filtering and washing. Then, the filter cake was added to 4000 L of a solution containing 36.67 kg of $Ga(NO_3)_3.9H_2O$ and 128.94 kg of $Zr(NO_3)_4.5H_2O$ dissolved to impregnate it with a gallium component and a zirconium component, the modified Y-type molecular sieve and the mixed solution containing $Ga(NO_3)_3$ and $Zr(NO_3)_4$ were stirred homogeneously, and allowed to stand at room temperature for an impregnation time of 24 h, and then the mixed slurry containing the modified Y-type molecular sieve, $Ga(NO_3)_3$ and $Zr(NO_3)_4$ was further stirred for 20 minutes to obtain a uniform mixture. Thereafter, the mixture was transferred to a rotary evaporator, and evaporated to dryness while rotating by heating slowly and uniformly. After that, the dried material was placed in a muffle furnace and calcined at 550° C. for 2.5 h to obtain a Y-type molecular sieve rich in secondary pores that had undergone a compound modification, designated as SZ1. Its physico-chemical properties are shown in Table 1.

After SZ1 was aged in a bare state at 800° C. under atmospheric pressure in an atmosphere of 100 vol % steam for 17 h, the relative crystallinity of the molecular sieve SZ1 before and after aging was analyzed by XRD, and the relative crystallinity retention after aging was calculated. The results are shown in Table 2, in which:

Relative crystallinity retention=(relative crystallinity of aged sample/relative crystallinity of fresh sample)×100%.

714.5 g of an aluminum sol having an alumina content of 21% by weight was added to 1565.5 g of deionized water, stirring was started, and 2763 g of kaolin having a solid content of 76% by weight was added and dispersed for 60 minutes. 2049 g of pseudo-boehmite having an alumina content of 61% by weight was added to 8146 g of deionized water, and 210 ml of 36% hydrochloric acid was added under stirring. After acidification for 60 minutes, the dispersed kaolin slurry was added, then 1500 g (dry basis) of finely ground SZ1 molecular sieve was added, and stirred evenly, followed by spray drying, washing, and drying to obtain a catalyst, designated as SC1. The SC1 catalyst thus obtained comprised 30% by weight of SZ1 molecular sieve, 42% by weight of kaolin, 25% by weight of pseudo-boehmite, and 3% by weight of aluminum sol.

Example 2

2000 kg (weight on a dry basis) NaY zeolite with a framework $SiO_2/Al_2O_3$ of 4.6 (sodium oxide content of 13.5 wt %, produced by Qilu Branch of Sinopec Catalyst Co., Ltd.) was added to a primary exchange tank containing 20 m$^3$ of deionized water, and stirred evenly at 90° C. Then, 800 L of $RECl_3$ solution (the rare earth concentration calculated on the basis of $RE_2O_3$ in the $RECl_3$ solution being 319 g/L) was added, stirred for 60 minutes, filtered and washed, and the filter cake was sent to a flash drying oven for drying; a rare earth modified Y-type molecular sieve having a normal lattice constant and a reduced sodium oxide content was obtained, which had a sodium oxide content of 5.5 wt %, a lattice constant of 2.471 nm, and a rare earth content of 11.3 wt % calculated on the basis of the oxide. Then, it was sent to a roaster, and roasted at a temperature (atmosphere temperature) of 450° C. in a 80% steam atmosphere for 5.5 hours; then, the molecular sieve material was introduced into a roaster for roasting and drying at a controlled temperature of 500° C. in a dry air atmosphere for 2 h, to obtain a Y-type molecular sieve having a reduced lattice constant and a water content of less than 1% by weight, of which the lattice constant was 2.461 nm. Then, the Y-type molecular sieve having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: a weight ratio of $SiCl_4$:Y zeolite of 0.25:1, a molecular sieve feed rate of 800 kg/h, and a reaction temperature of 490° C. The molecular sieve material obtained after the gas phase ultra-stabilization was separated by a gas-solid separator and sent to a secondary exchange tank containing 20 m$^3$ of water added in advance, and stirred evenly. The weight of the molecular sieve material added to the secondary exchange tank was 2000 kg (weight on a dry basis). Thereafter, 0.9 m$^3$ of 7 wt % sulfuric acid solution was slowly added, and the reaction mixture was heated to 93° C., followed by stirring for 80 min; then, 70 kg of citric acid and 50 kg of tartaric acid were added, and stirring was continued at 93° C. for 70 min, followed by filtering and washing. Then, the molecular sieve cake was directly added to a solution containing diammonium hydrogen phosphate, with the molecular sieve being added in an amount such that the weight ratio of phosphorus (on the basis of $P_2O_5$) to the molecular sieve was 0.03, and the weight ratio of water to the molecular sieve was 3.0, and the reaction was conducted at 60° C. for 50 min, followed by filtering and washing. Then, the filter cake was added to 4,500 L of a solution containing 74.41 kg of $Ga(NO_3)_3 \cdot 9H_2O$ and 71.63 kg of $Zr(NO_3)_4 \cdot 5H_2O$ dissolved to impregnate it with a gallium component and a zirconium component, the modified Y-type molecular sieve and the mixed solution containing $Ga(NO_3)_3$ and $Zr(NO_3)_4$ were stirred homogeneously, and allowed to stand at room temperature for an impregnation time of 24 h, and then the mixed slurry containing the modified Y-type molecular sieve, $Ga(NO_3)_3$ and $Zr(NO_3)_4$ was further stirred for 20 min to obtain a uniform mixture. Thereafter, the mixture was transferred to a rotary evaporator and evaporated to dryness while rotating by heating slowly and uniformly. After that, the dried material was placed in a muffle furnace and calcined at 500° C. for 3 hours to obtain a Y-type molecular sieve rich in secondary pores that had undergone a compound modification, designated as SZ2. Its physico-chemical properties are shown in Table 1.

After SZ2 was aged in a bare state at 800° C. in an atmosphere of 100 vol % steam for 17 h, the crystallinity of the molecular sieve SZ2 before and after aging was analyzed by XRD, and the relative crystallinity retention after aging was calculated. The results are shown in Table 2.

A catalytic cracking catalyst was prepared in accordance with the method described in Example 1: the SZ2 molecular sieve, kaolin, water, pseudo-boehmite binder, and aluminum sol were slurried, and spray-dried according to the method conventionally used for preparing a catalytic cracking catalyst, to obtain a microsphere catalyst. The catalytic cracking catalyst obtained was designated as SC2. The SC2 catalyst obtained comprised 30% by weight of SZ2 molecular sieve, 42% by weight of kaolin, 25% by weight of pseudo-boehmite, and 3% by weight of aluminum sol.

Example 3

2000 kg (weight on a dry basis) of NaY zeolite with a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m$^3$ of deionized water, and stirred evenly at 95° C. 570 L of $RECl_3$ solution (the rare earth concentration calculated on the basis of $RE_2O_3$ in the $RECl_3$ solution being 319 g/L) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.5% by weight, a lattice constant of 2.471 nm, and a rare earth content of 8.5 wt % calculated on the basis of the oxide. Then, it was sent to a roaster for hydrothermal modification by roasting at a temperature of 470° C. in an atmosphere comprising 70% by volume of steam for 5 h; then, the molecular sieve material was introduced into a roaster for roasting and drying at a controlled temperature of 500° C. in a dry air atmosphere for 1.5 h, to obtain a Y-type molecular sieve having a reduced lattice constant and a water content of less than 1% by weight, of which the lattice constant was 2.458 nm. Then, the Y-type molecular sieve material having a reduced lattice constant was sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y-type zeolite was 0.45:1, the feed rate of the molecular sieve was 800 kg/h and the reaction temperature was 400° C. The molecular sieve material obtained after the gas phase ultra-stabilization was separated by a gas-solid separator and sent to a secondary exchange tank containing 20 m³ of deionized water added in advance, and stirred evenly. The weight of the molecular sieve material added to the secondary exchange tank was 2000 kg (weight on a dry basis). Thereafter, 1.2 m³ of 5 wt % nitric acid solution was slowly added, and the reaction mixture was heated to 95° C., and stirred for 90 minutes; then, 90 kg of citric acid and 40 kg of oxalic acid were added, and the mixture was stirred at 93° C. for 70 minutes, and then filtered and washed. The molecular sieve cake was directly added to a solution containing ammonium phosphate, with the molecular sieve being added in an amount such that the weight ratio of phosphorus (on the basis of $P_2O_5$) to the molecular sieve was 0.015, and the weight ratio of water to the molecular sieve was 2.8, and the reaction was conducted at 70° C. for 30 min, followed by filtering and washing. Then, the filter cake was added to 4800 L of a solution containing 110.03 kg of $Ga(NO_3)_3 \cdot 9H_2O$ and 43.1 kg of $Zr(NO_3)_4 \cdot 5H_2O$ dissolved to impregnate it with a gallium component and a zirconium component, the modified Y-type molecular sieve and the mixed solution containing $Ga(NO_3)_3$ and $Zr(NO_3)_4$ were stirred homogeneously, and allowed to stand at room temperature for an impregnation time of 24 h, and then the mixed slurry containing the modified Y-type molecular sieve, $Ga(NO_3)_3$ and $Zr(NO_3)_4$ was further stirred for 20 min to obtain a uniform mixture. Thereafter, the mixture was transferred to a rotary evaporator and evaporated to dryness while rotating by heating slowly and uniformly. After that, the dried material was placed in a muffle furnace and calcined at 600° C. for 2 hours to obtain a Y-type molecular sieve rich in secondary pores that had undergone a compound modification, designated as SZ3. Its physico-chemical properties are shown in Table 1.

After SZ3 was aged in a bare state at 800° C. in an atmosphere of 100 vol % steam for 17 h, the crystallinity of the molecular sieve SZ3 before and after aging was analyzed by XRD, and the relative crystallinity retention after aging was calculated. The results are shown in Table 2.

A catalytic cracking catalyst was prepared in accordance with the method described in Example 1: the SZ3 molecular sieve, kaolin, water, pseudo-boehmite binder and aluminum sol were slurried, and spray dried according to the method conventionally used for preparing a catalytic cracking catalyst, to obtain a microsphere catalyst. The catalytic cracking catalyst obtained was designated as SC3. The SC3 catalyst obtained comprised 30% by weight of SZ3 molecular sieve, 42% by weight of kaolin, 25% by weight of pseudo-boehmite, and 3% by weight of aluminum sol.

Example 4

2000 kg (weight on a dry basis) NaY zeolite having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m³ of water and stirred evenly at 25° C. Then, 600 L of $RECl_3$ solution (the rare earth concentration calculated on the basis of $RE_2O_3$ in the $RECl_3$ solution being 319 g/L) was added, stirring was continued for 60 minutes, filtered, washed, and the filter cake was sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster, and roasted at a temperature of 365° C., in a 30% steam atmosphere (an atmosphere comprising 30% by volume of steam) for 4.5 hours; then, roasted at a temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.460 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A, under the following conditions: the weight ratio of $SiCl_4$: Y-type zeolite was 0.2:1, the feed rate of the molecular sieve was 800 kg/h and the reaction temperature was 250° C. The molecular sieve material obtained after the gas phase ultra-stabilization was separated by a gas-solid separator, sent to a secondary exchange tank containing 20 m³ of water added in advance, and stirred evenly. The weight of the molecular sieve material added to the secondary exchange tank was 2000 kg (weight on a dry basis). Thereafter, 0.2 m³ of 10 wt % hydrochloric acid was added, and the reaction mixture was heated to 85° C., and stirred for 60 minutes, followed by filtering and washing. After that, the molecular sieve cake was directly added to a solution containing ammonium phosphate, with the molecular sieve being added in an amount such that the weight ratio of phosphorus (calculated on the basis of $P_2O_5$) to the molecular sieve was 0.055:1, and the weight ratio of water to the molecular sieve was 2.5, and the reaction was conducted at 50° C. for 60 min, followed by filtering and washing. Then, the filter cake was added to 4000 L of a solution containing 36.67 kg of $Ga(NO_3)_3 \cdot 9H_2O$ and 128.94 kg of $Zr(NO_3)_4 \cdot 5H_2O$ dissolved to impregnate it with a gallium component and a zirconium component, the modified Y-type molecular sieve and the mixed solution containing $Ga(NO_3)_3$ and $Zr(NO_3)_4$ were stirred homogeneously, and allowed to stand at room temperature for an impregnation time of 24 h, and then the mixed slurry containing the modified Y-type molecular sieve, $Ga(NO_3)_3$ and $Zr(NO_3)_4$ was further stirred for 20 min to obtain a uniform mixture. Thereafter, the mixture was transferred to a rotary evaporator and evaporated to dryness while rotating by heating slowly and uniformly. After that, the dried material was placed in a muffle furnace and calcined at 550° C. for 2.5 h, to obtain a modified Y-type molecular sieve product, designated as SZ4. Its physico-chemical properties are shown in Table 1.

After SZ4 was aged in a bare state at 800° C. under atmospheric pressure in an atmosphere of 100 vol % steam for 17 hours, the relative crystallinity of the molecular sieve SZ4 before and after aging was analyzed by XRD, and the relative crystallinity retention after aging was calculated. The results are shown in Table 2.

A catalytic cracking catalyst was prepared in accordance with the method described in Example 1: the SZ4 molecular sieve, kaolin, water, pseudo-boehmite binder and aluminum sol were slurried, and spray dried according to the method conventionally used for preparing a catalytic cracking catalyst, to obtain a microsphere catalyst. The catalytic cracking catalyst obtained was designated as SC4. The SC4 catalyst obtained comprised 30% by weight of SZ4 molecular sieve, 42% by weight of kaolin, 25% by weight of pseudo-boehmite, and 3% by weight of aluminum sol.

Comparative Examples 1 to 8 below are directed to the preparation of modified Y-type molecular sieves and catalytic cracking catalysts different from those provided in the present application.

Comparative Example 1

2000 g of NaY molecular sieve (dry basis) was added to 20 liters of deionized water, stirred evenly, and 1000 g of $(NH_4)_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in a 100% steam atmosphere for 5 hours. Then, the resultant was added to 20 liters of deionized water, stirred evenly, and 1000 g of $(NH_4)_2SO_4$ was added thereto, stirred, and heated to 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve free of rare earth that had undergone two stages of ion-exchange and two stages of hydrothermal ultra-stabilization, designated as DZ1. The composition and physico-chemical properties of DZ1 are shown in Table 1.

After DZ1 was aged in a bare state at 800° C. in an atmosphere of 100 vol % steam for 17 h, the crystallinity of the molecular sieve DZ1 before and after aging was analyzed by XRD, and the relative crystallinity retention after aging was calculated. The results are shown in Table 2.

The DZ1 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC1 (see the method described in Example 1). The DC1 catalyst obtained comprised 30% by weight of DZ1 molecular sieve, 42% by weight of kaolin, 25% by weight of pseudo-boehmite, and 3% by weight of aluminum sol.

Comparative Example 2

2000 g of NaY molecular sieve (dry basis) was added to 20 liters of deionized water, stirred evenly, and 1000 g of $(NH_4)_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in 100% steam atmosphere for 5 hours. Then, the resultant was added to 20 liters of deionized water, stirred evenly, 200 ml of $RE(NO_3)_3$ solution (concentration of 319 g/L on the basis of $RE_2O_3$) and 900 g $(NH_4)_2SO_4$ were added thereto, stirred and heated 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve containing rare earth that had undergone two stages of ion-exchange and two stages of hydrothermal ultra-stabilization, designated as DZ2. Its physico-chemical properties are shown in Table 1.

After DZ2 was aged in a bare state at 800° C. in an atmosphere of 100 vol % steam for 17 h, the crystallinity of the molecular sieve DZ2 before and after aging was analyzed by XRD, and the relative crystallinity retention after aging was calculated. The results are shown in Table 2.

The DZ2 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC2 (see the method described in Example 1). The DC2 catalyst obtained comprised, on a dry basis, 30% by weight of DZ2 molecular sieve, 42% by weight of kaolin, 25% by weight of pseudo-boehmite, and 3% by weight of aluminum sol.

Comparative Example 3

2000 kg NaY molecular sieve (dry basis) was added to 20 $m^3$ of water, stirred evenly, 650 L of $RE(NO_3)_3$ solution (319 g/L) was added thereto, stirred, and heated to 90-95° C. for 1 hour. Then, the mixture was filtered and washed, and the filter cake was sent to a flash roaster for roasting and drying at a controlled temperature of 500° C. in a dry air atmosphere for 2 hours, so that the water content was reduced to less than 1% by weight. Then, the dried molecular sieve material was sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method described in Example 1 of the Patent Application Publication No. CN103787352A under the following conditions: the weight ratio of $SiCl_4$:Y-type zeolite was 0.4:1, the feed rate of the molecular sieve was 800 kg/h and the reaction temperature was 580° C. The molecular sieve material obtained after the gas phase ultra-stabilization was separated by a gas-solid separator, sent to a secondary exchange tank containing 20 $m^3$ of water added in advance, and stirred evenly. The weight of the molecular sieve material added to the secondary exchange tank was 2000 kg (weight on a dry basis). After that, 1.2 $m^3$ of 5 wt % nitric acid was slowly added, heated to 95° C., and stirring was continued for 90 minutes; then, 90 kg of citric acid and 40 kg of oxalic acid were added, and stirring was continued at 93° C. for 70 minutes, followed by filtering, and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.015, and the weight ratio of water to the molecular sieve was 2.8, and the reaction was conducted at 70° C. for 30 min, followed by filtering, washing, and drying, to obtain a molecular sieve, designated as DZ3. Its physico-chemical properties are shown in Table 1.

After DZ3 was aged in a bare state at 800° C. in an atmosphere of 100 vol % steam for 17 h, the crystallinity of the molecular sieve DZ3 before and after aging was analyzed by XRD, and the relative crystallinity retention after aging was calculated. The results are shown in Table 2.

The DZ3 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC3 (see the method described in Example 1). The DC3 catalyst obtained comprised 30% by weight of DZ3 molecular sieve, 42% by weight of kaolin, 25% by weight of pseudo-boehmite, and 3% by weight of aluminum sol.

Comparative Example 4

2000 kg (weight on a dry basis) NaY zeolite having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m³ of water and stirred evenly at 25° C. Then, 600 L of $RECl_3$ solution (the rare earth concentration calculated on the basis of $RE_2O_3$ in the $RECl_3$ solution being 319 g/L) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y zeolite was 0.5:1, the feed rate of the molecular sieve was 800 kg/h, and the reaction temperature was 400° C. The molecular sieve material obtained after the gas phase ultra-stabilization was separated by a gas-solid separator, sent to a secondary exchange tank containing 20 m³ of water added in advance, and stirred evenly. The weight of the molecular sieve material added to the secondary exchange tank was 2000 kg (weight on a dry basis). Thereafter, 0.6 m³ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.04, and the weight ratio of water to the molecular sieve was 2.5, and the reaction was conducted at 50° C. for 60 min, followed by filtering and washing, and the filter cake was dried at 120° C., to obtain a modified Y molecular sieve, designated as DZ4. Its physico-chemical properties are shown in Table 1. After DZ4 was aged in a bare state at 800° C. in an atmosphere of 100 vol % steam for 17 h, the crystallinity of the molecular sieve DZ4 before and after aging was analyzed by XRD and the relative crystallinity retention after aging was calculated. The results are shown in Table 2.

The DZ4 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC4 (see the method described in Example 1). The DC4 catalyst obtained comprised 30% by weight of DZ4 molecular sieve, 42% by weight of kaolin, 25% by weight of pseudo-boehmite, and 3% by weight of aluminum sol.

Comparative Example 5

2000 kg (weight on a dry basis) NaY zeolite having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m³ of water and stirred evenly at 25° C. Then, 600 L of $RECl_3$ solution (the rare earth concentration calculated on the basis of $RE_2O_3$ in the $RECl_3$ solution being 319 g/L) was added, stirred for 60 min, filtered, washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8 wt % calculated on the basis of the oxide. Then, it was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y zeolite was 0.5:1, the feed rate of the molecular sieve was 800 kg/h, and the reaction temperature was 400° C. The molecular sieve material obtained after the gas phase ultra-stabilization was separated by a gas-solid separator, sent to a secondary exchange tank containing 20 m³ of water added in advance, and stirred evenly. The weight of the molecular sieve material added to the secondary exchange tank was 2000 kg (weight on a dry basis). Thereafter, 0.6 m³ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.04, and the weight ratio of water to the molecular sieve was 2.5, and the reaction was conducted at 50° C. for 60 min, followed by filtering and washing. Then, the filter cake was added to 4000 L of a mixed solution containing 267.5 kg of Ga(NO$_3$)$_3$.9H$_2$O and 195.51 kg of Zr(NO$_3$)$_4$.5H$_2$O dissolved to impregnate it with a gallium component and a zirconium component, and the modified Y-type molecular sieve and the mixed solution containing Ga(NO$_3$)$_3$ and Zr(NO$_3$)$_4$ were stirred homogeneously, and allowed to stand at room temperature for an impregnation time of 24 h, and then the mixed slurry containing the modified Y-type molecular sieve, Ga(NO$_3$)$_3$ and Zr(NO$_3$)$_4$ was further stirred for 20 minutes to obtain a uniform mixture. Thereafter, the mixture was transferred to a rotary evaporator, and evaporated to dryness while rotating by heating slowly and uniformly. After that, the dried material was placed in a muffle furnace and calcined at 550° C. for 2.5 h, to obtain a Y-type molecular sieve rich in secondary pores that had undergone a compound modification, designated as DZ5. Its physico-chemical properties are shown in Table 1.

After DZ5 was aged in a bare state at 800° C. under atmospheric pressure in an atmosphere of 100 vol % steam for 17 h, the relative crystallinity of the molecular sieve DZ5 before and after aging was analyzed by XRD, and the relative crystallinity retention after aging was calculated. The results are shown in Table 2.

The DZ5 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC5 (see the method described in Example 1). The DC5 catalyst obtained comprised 30% by weight of DZ5 molecular sieve, 42% by weight of kaolin, 25% by weight of pseudo-boehmite, and 3% by weight of aluminum sol.

Comparative Example 6

2000 kg (weight on a dry basis) NaY zeolite having a framework SiO$_2$/Al$_2$O$_3$ of 4.6 (sodium oxide content of 13.5% by weight, produced by Qilu Branch of Sinopec Catalyst Co., Ltd.) was added to a primary exchange tank containing 20 m$^3$ of water and stirred evenly at 25° C. Then, 600 L of RECl$_3$ solution (the rare earth concentration calculated on the basis of RE$_2$O$_3$ in the RECl$_3$ solution being 319 g/L) was added, stirring was continued for 60 minutes, filtered, washed, and the filter cake was sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster, and roasted at a temperature of 390° C. in an atmosphere of 50% steam (an atmosphere comprising 50% by volume of steam) for 6 h; then, roasted at a temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A, under the following conditions: the weight ratio of SiCl$_4$: Y-type zeolite was 0.5:1, the feed rate of the molecular sieve was 800 kg/h and the reaction temperature was 400° C. The molecular sieve material obtained after the gas phase ultra-stabilization was washed with 20 m$^3$ of deionized water, filtered, and then the filter cake was added to 4000 L of a solution containing 36.67 kg of Ga(NO$_3$)$_3$.9H$_2$O and 128.94 kg of Zr(NO$_3$)$_4$.5H$_2$O dissolved to impregnate it with a gallium component and a zirconium component, the modified Y-type molecular sieve and the mixed solution containing Ga(NO$_3$)$_3$ and Zr(NO$_3$)$_4$ were stirred homogeneously, and allowed to stand at room temperature for an impregnation time of 24 hours. Then, the mixed slurry containing the modified Y-type molecular sieve, Ga(NO$_3$)$_3$ and Zr(NO$_3$)$_4$ was further stirred for 20 minutes to obtain a uniform mixture. Thereafter, the mixture was transferred to a rotary evaporator and evaporated to dryness while rotating by heating slowly and uniformly. After that, the dried material was placed in a muffle furnace and calcined at 550° C. for 2.5 h, to obtain a modified Y-type molecular sieve product, designated as DZ6. Its physico-chemical properties are shown in Table 1.

After DZ6 was aged in a bare state at 800° C. under atmospheric pressure in an atmosphere of 100 vol % steam for 17 h, the relative crystallinity of the molecular sieve DZ6 before and after aging was analyzed by XRD, and the relative crystallinity retention after aging was calculated. The results are shown in Table 2.

The DZ6 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC6 (see the method described in Example 1). The DC6 catalyst obtained comprised 30% by weight of DZ6 molecular sieve, 42% by weight of kaolin, 25% by weight of pseudo-boehmite, and 3% by weight of aluminum sol.

Comparative Example 7

2000 kg (weight on a dry basis) NaY zeolite having a framework SiO$_2$/Al$_2$O$_3$ of 4.6 (sodium oxide content of 13.5% by weight, produced by Qilu Branch of Sinopec Catalyst Co., Ltd.) was added to a primary exchange tank containing 20 m$^3$ of water and stirred evenly at 25° C. Then, 600 L of RECl$_3$ solution (the rare earth concentration calculated on the basis of RE$_2$O$_3$ in the RECl$_3$ solution being 319 g/L) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y zeolite was 0.5:1, the feed rate of the molecular sieve was 800 kg/h, and the reaction temperature was 400° C. The molecular sieve material obtained after the gas phase ultra-stabilization was separated by a gas-solid separator, sent to a secondary exchange tank containing 20 m$^3$ of water added in advance, and stirred evenly. The weight of the molecular sieve material added to the secondary exchange tank was 2000 kg (weight on a dry basis). Thereafter, 0.6 m$^3$ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.04, and the weight ratio of water to the molecular sieve was 2.5, and the reaction was conducted at 50° C. for 60 min, followed by filtering and washing. Then, the filter cake was added to 4000 L of a solution containing 60.88 kg of $Zr(NO_3)_4.5H_2O$ dissolved to impregnate it with a zirconium component, the modified Y-type molecular sieve and the solution containing $Zr(NO_3)_4$ were stirred homogeneously, and allowed to stand at room temperature for an impregnation time of 24 h, and then the slurry containing the modified Y-type molecular sieve and $Zr(NO_3)_4$ was further stirred for 20 min to obtain a uniform mixture. Thereafter, the mixture was transferred to a rotary evaporator, and evaporated to dryness while rotating by heating slowly and uniformly. After that, the dried material was placed in a muffle furnace and calcined at 550° C. for 2.5 h to obtain a Y-type molecular sieve rich in secondary pores that had undergone a compound modification, designated as DZ7. Its physicochemical properties are shown in Table 1.

After DZ7 was aged in a bare state at 800° C., under atmospheric pressure, in an atmosphere of 100 vol % steam for 17 hours, the relative crystallinity of the molecular sieve DZ7 before and after aging was analyzed by XRD, and the relative crystallinity retention after aging was calculated. The results are shown in Table 2.

The DZ7 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC7 (see the method described in Example 1). The DC7 catalyst obtained comprised 30% by weight of DZ7 molecular sieve, 42% by weight of kaolin, 25% by weight of pseudo-boehmite, and 3% by weight of aluminum sol.

Comparative Example 8

2000 kg (weight on a dry basis) NaY zeolite having a framework $SiO_2/Al_2O_3$ of 4.6 (sodium oxide content of 13.5% by weight, produced by Qilu Branch of Sinopec Catalyst Co., Ltd.) was added to a primary exchange tank containing 20 m$^3$ of water and stirred evenly at 25° C. Then, 600 L of $RECl_3$ solution (the rare earth concentration calculated on the basis of $RE_2O_3$ in the $RECl_3$ solution being 319 g/L) was added, stirred for 60 minutes, filtered and washed, and the filter cake was continuously sent to a flash drying oven for drying; a rare earth modified Y-type molecular sieve having a normal lattice constant and a reduced sodium oxide content was obtained, which had a sodium oxide content of 7.0% by weight, a lattice constant of 2.471 nm, and a rare earth content of 8.8% by weight on the basis of the oxide. Then, it was sent to a roaster for modification by roasting at a controlled temperature of 390° C. in an atmosphere of 50% steam (an atmosphere comprising 50% by volume of steam) for 6 hours; then, the molecular sieve material was introduced into a roaster for roasting and drying at a controlled temperature of 500° C. in a dry air atmosphere (comprising less than 1% by volume of steam) for 2.5 h, to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization. The gas phase ultra-stabilization process of the molecular sieve in the continuous gas phase ultra-stabilization reactor and the subsequent exhaust gas absorption process were carried out in accordance with the method disclosed in Example 1 of the Patent Application Publication No. CN 103787352 A under the following conditions: the weight ratio of $SiCl_4$:Y zeolite was 0.5:1, the feed rate of the molecular sieve was 800 kg/h, and the reaction temperature was 400° C. The molecular sieve material obtained after the gas phase ultra-stabilization was separated by a gas-solid separator, sent to a secondary exchange tank containing 20 m$^3$ of water added in advance, and stirred evenly. The weight of the molecular sieve material added to the secondary exchange tank was 2000 kg (weight on a dry basis). Thereafter, 0.6 m$^3$ of 10 wt % hydrochloric acid was slowly added, the reaction mixture was heated to 90° C., and stirring was continued for 60 minutes; then, 140 kg of citric acid was added, and stirring was continued at 90° C. for 60 minutes, followed by filtering and washing. After that, the molecular sieve cake was directly added to a solution containing ammonium phosphate, with the molecular sieve being added in an amount such that the weight ratio of phosphorus (on the basis of $P_2O_5$) to the molecular sieve was 0.04, and the weight ratio of water to the molecular sieve was 2.5, and the reaction was conducted at 50° C. for 60 min, followed by filtering and washing. Then, the filter cake was added to 4000 L of a solution containing 71.33 kg of $Ga(NO_3)_3.9H_2O$ dissolved to impregnate it with a gallium component, the modified Y-type molecular sieve and the solution containing $Ga(NO_3)_3$ were stirred homogeneously, and allowed to stand at room temperature for an impregnation time of 24 h, and then the slurry containing the modified Y-type molecular sieve and $Ga(NO_3)_3$ was further stirred for 20 minutes to obtain a uniform mixture. Thereafter, the mixture was transferred to a rotary evaporator, and evaporated to dryness while rotating by heating slowly and uniformly. After that, the dried material was placed in a muffle furnace and calcined at 550° C. for 2.5 h to obtain a Y-type molecular sieve rich in secondary pores that had undergone a compound modification, designated as DZ8. Its physicochemical properties are shown in Table 1.

After DZ8 was aged in a bare state at 800° C. under atmospheric pressure in an atmosphere of 100 vol % steam for 17 h, the relative crystallinity of the molecular sieve DZ8 before and after aging was analyzed by XRD, and the relative crystallinity retention after aging was calculated. The results are shown in Table 2.

The DZ8 molecular sieve, kaolin, water, pseudo-boehmite binder, and aluminum sol were slurried, and spray-dried according to the method conventionally used for preparing a catalytic cracking catalyst, to obtain a microsphere catalyst, designated as DC8 (see the method described in Example 1). The DC8 catalyst obtained comprised 30% by weight of DZ8 molecular sieve, 42% by weight of kaolin, 25% by weight of pseudo-boehmite, and 3% by weight of aluminum sol.

Comparative Example 9

The conventional FCC catalyst employed in Example 1 of the Chinese Patent Application Publication No. CN 104560187 A was used in this comparative example, which was designated as DC9.

Test Examples 1-4

The catalytic cracking catalysts obtained in Examples 1-4 were tested, respectively, for their catalytic cracking performances.

The cracking performance for processing hydrogenated LCOs was evaluated as follows: the SC1-SC4 catalysts were first aged at 800° C. in an atmosphere of 100 vol % steam for 12 h, and then evaluated on a small fixed fluidized bed reactor (ACE); the feedstock oil was SJZHLCO (Hydrogenated LCO) (its properties are shown in Table 3); and the reaction temperature was 500° C. The results are shown in Table 4.

Effective conversion rate of LCO/%=100−diesel oil yield−dry gas yield−coke yield−heavy oil yield.

Comparative Test Examples 1-9

The catalytic cracking catalysts DC1-DC8 obtained by the methods provided in Comparative Examples 1-8 and the conventional FCC catalyst DC9 of Comparative Example 9 were tested, respectively, for their catalytic cracking performances.

The DC1-DC9 catalysts were first aged at 800° C. in an atmosphere of 100 vol % steam for 12 h, and then evaluated on a small fixed fluidized bed reactor (ACE) for their catalytic cracking performances for processing hydrogenated LCOs. The evaluation method is shown in the Test Example 1, the properties of the feedstock used in the ACE test are shown in Table 3, and the results are shown in Table 4.

Effective conversion rate of LCO/%=100−diesel oil yield−dry gas yield−coke yield−heavy oil yield.

TABLE 1

Properties of the molecular sieves obtained in Examples 1-4 and Comparative Examples 1-8

| Example No. | Ex. 1 | Ex. 2 | Ex. 3 | Ex. 4 | Comp. Ex. 1 | Comp. Ex. 2 |
|---|---|---|---|---|---|---|
| Name of molecular sieve | SZ1 | SZ2 | SZ3 | SZ4 | DZ1 | DZ2 |
| $RE_2O_3$ content/wt % | 5.6 | 8.5 | 6.3 | 5.3 | 0 | 2.7 |
| $Na_2O$ content/wt % | 0.09 | 0.14 | 0.12 | 0.08 | 1.3 | 1.5 |
| $Ga_2O_3$ content/wt % | 0.39 | 0.8 | 1.2 | 0.39 | 0 | 0 |
| $ZrO_2$ content/wt % | 1.8 | 1.0 | 0.6 | 1.8 | — | — |
| $P_2O_5$ content/wt % | 3.55 | 2.89 | 1.38 | 5.3 | — | — |
| Total $SiO_2/Al_2O_3$ molar ratio | 10.84 | 8.22 | 9.98 | 7.62 | 4.94 | 4.85 |
| Framework $SiO_2/Al_2O_3$ molar | 11.95 | 8.79 | 10.87 | 8.45 | 10.39 | 7.83 |
| Framework aluminum/Total aluminum × 100 | 90.7 | 93.5 | 91.8 | 90.2 | 47.59 | 61.99 |
| Non-framework aluminum/Total aluminum × 100 | 9.3 | 6.5 | 8.2 | 9.8 | 52.41 | 38.01 |
| Lattice constant/nm | 2.442 | 2.45 | 2.445 | 2.451 | 2.446 | 2.453 |
| Crystallinity/% | 70.4 | 71.8 | 75.4 | 71.2 | 60.1 | 59.5 |
| Lattice collapse temperature/° C. | 1082 | 1065 | 1077 | 1081 | 1038 | 1020 |
| Specific surface area/($m^2$/g) | 646 | 667 | 654 | 647 | 615 | 598 |
| Total pore volume/(mL/g) | 0.413 | 0.395 | 0.384 | 0.415 | 0.349 | 0.322 |
| Micropore volume/(mL/g) | 0.258 | 0.278 | 0.273 | 0.275 | 0.255 | 0.249 |
| Pore volume of secondary pores/(mL/g) | 0.155 | 0.117 | 0.111 | 0.140 | 0.094 | 0.073 |
| Percentage of pore volume of secondary pores having a pore size of 2.0-100 nm to total pore volume/% | 37.53 | 29.62 | 28.90 | 33.73 | 26.93 | 22.67 |
| B acid/L acid (strong acid content ratio) | 4.08 | 5.11 | 4.62 | 3.84 | 0.52 | 0.83 |

| Example No. | Comp. Ex. 3 | Comp. Ex. 4 | Comp. Ex. 5 | Comp. Ex. 6 | Comp. Ex. 7 | Comp. Ex. 8 |
|---|---|---|---|---|---|---|
| Name of molecular sieve | DZ3 | DZ4 | DZ5 | DZ6 | DZ7 | DZ8 |
| $RE_2O_3$ content/wt % | 6.2 | 5.6 | 5.3 | 5.5 | 5.4 | 5.5 |
| $Na_2O$ content/wt % | 0.79 | 0.09 | 0.07 | 0.49 | 0.08 | 0.08 |
| $Ga_2O_3$ content/wt % | 0 | — | 2.9 | 0.39 | — | 0.79 |
| $ZrO_2$ content/wt % | — | — | 2.8 | 1.8 | 0.85 | — |
| $P_2O_5$ content/wt % | 1.38 | 3.55 | 3.55 | — | 3.55 | 3.55 |
| Total $SiO_2/Al_2O_3$ molar ratio | 10.67 | 10.84 | 10.84 | 9.74 | 10.83 | 10.84 |
| Framework $SiO_2/Al_2O_3$ molar | 11.39 | 11.95 | 11.95 | 11.95 | 11.95 | 11.95 |
| Framework aluminum/Total aluminum × 100 | 93.65 | 90.7 | 90.7 | 81.5 | 90.7 | 90.7 |

TABLE 1-continued

Properties of the molecular sieves obtained in Examples 1-4 and Comparative Examples 1-8

| | | | | | | |
|---|---|---|---|---|---|---|
| Non-framework aluminum/Total aluminum × 100 | 6.35 | 9.3 | 9.3 | 18.5 | 9.3 | 9.3 |
| Lattice constant/nm | 2.444 | 2.442 | 2.442 | 2.443 | 2.442 | 2.442 |
| Crystallinity/% | 58.1 | 70.4 | 70.0 | 63.1 | 70.2 | 70.5 |
| Lattice collapse temperature/° C. | 1047 | 1082 | 1075 | 1072 | 1080 | 1083 |
| Specific surface area/(m²/g) | 645 | 646 | 634 | 635 | 642 | 645 |
| Total pore volume/(mL/g) | 0.329 | 0.413 | 0.398 | 0.354 | 0.403 | 0.411 |
| Micropore volume/(mL/g) | 0.309 | 0.258 | 0.253 | 0.280 | 0.255 | 0.257 |
| Pore volume of secondary pores/(mL/g) | 0.020 | 0.155 | 0.145 | 0.074 | 0.148 | 0.154 |
| Percentage of pore volume of secondary pores having a pore size of 2.0-100 nm to total pore volume/% | 6.08 | 37.53 | 36.43 | 20.90 | 36.72 | 37.47 |
| B acid/L acid (strong acid content ratio) | 2.71 | 3.17 | 3.85 | 3.35 | 3.68 | 4.01 |

It can be seen from Table 1 that the highly stable modified Y-type molecular sieve provided in the present application has the following advantages: a low sodium oxide content, a relatively lower non-framework aluminum content at a relatively higher silica-alumina ratio, a relatively higher percentage of the pore volume of secondary pores having a pore size of 2.0-100 nm to the total pore volume, a relatively higher B acid/L acid ratio (the ratio of strong B acid content to strong L acid content), a relatively higher crystallinity when the molecular sieve has a relatively smaller lattice constant and a relatively higher rare earth content, and a high thermal stability.

It can be seen from Table 2 that, after being aged in a bare state under severe conditions at 800° C. for 17 hours, samples of the modified Y-type molecular sieve provided in the present application show a relatively higher relative crystallinity retention, which indicates that the modified Y-type molecular sieve provided in the present application has a high hydrothermal stability.

TABLE 2

Aging test of the molecular sieves obtained in Examples 1-4 and Comparative Examples 1-8

| Example No. | Name of molecular sieve | Relative crystallinity of fresh molecular sieve sample (%) | Relative crystallinity of aged molecular sieve sample (%) (800° C./aged for 17 hours) | Relative crystallinity retention/% |
|---|---|---|---|---|
| Ex. 1 | SZ1 | 70.4 | 40.50 | 57.53 |
| Ex. 2 | SZ2 | 71.8 | 37.26 | 51.89 |
| Ex. 3 | SZ3 | 75.4 | 44.16 | 58.57 |
| Ex. 4 | SZ4 | 71.2 | 40.62 | 57.05 |
| Comp. Ex. 1 | DZ1 | 60.1 | 4.30 | 7.15 |
| Comp. Ex. 2 | DZ2 | 59.5 | 5.90 | 9.92 |
| Comp. Ex. 3 | DZ3 | 58.1 | 21.01 | 36.16 |
| Comp. Ex. 4 | DZ4 | 70.4 | 40.37 | 57.34 |
| Comp. Ex. 5 | DZ5 | 70 | 36.25 | 51.78 |
| Comp. Ex. 6 | DZ6 | 63.1 | 27.98 | 44.34 |
| Comp. Ex. 7 | DZ7 | 70.2 | 31.96 | 45.53 |
| Comp. Ex. 8 | DZ8 | 70.5 | 40.46 | 57.39 |

TABLE 3

Properties of the hydrogenated LCO (SJZHLCO)

| Item | Value |
|---|---|
| Carbon content/% | 88.91 |
| Hydrogen content/% | 11.01 |
| Density at 20° C. (kg/m³) | 910.7 |
| Hydrocarbon composition (by mass), determined by mass spectrometry/% | |
| Paraffins | 10.1 |
| Total naphthenes | 16.9 |
| Total monocyclic aromatics | 60.3 |
| Total bicyclic aromatics | 11.5 |
| Tricyclic aromatics | 1.2 |
| Total aromatics | 73 |
| Colloid | 0 |
| Total weight | 100 |
| Nitrogen content/mg/L | 0.9 |
| Sulfur content/mg/L | 49 |

TABLE 4

Results of Test Examples 1-4 and Comparative Test Examples 1-9

| Test Example No. | Test Ex. 1 | Test Ex. 2 | Test Ex. 3 | Test Ex. 4 | Comp. Test Ex. 1 | Comp Test Ex. 2 | Comp. Test Ex. 3 | Comp. Test Ex. 4 | Comp. Test Ex. 5 | Comp. Test Ex. 6 | Comp. Test Ex. 7 | Comp. Test Ex. 8 | Comp. Test Ex. 9 |
|---|---|---|---|---|---|---|---|---|---|---|---|---|---|
| Name of catalyst | SC1 | SC2 | SC3 | SC4 | DC1 | DC2 | DC3 | DC4 | DC5 | DC6 | DC7 | DC8 | DC9 |
| Catalyst-to-oil ratio | 5 | 5 | 5 | 5 | 9 | 8 | 5 | 5 | 5 | 5 | 5 | 5 | 5 |
| Reaction temperature/° C. | 500 | 500 | 500 | 500 | 500 | 500 | 500 | 500 | 500 | 500 | 500 | 500 | 500 |

TABLE 4-continued

Results of Test Examples 1-4 and Comparative Test Examples 1-9

| Test Example No. | Test Ex. 1 | Test Ex. 2 | Test Ex. 3 | Test Ex. 4 | Comp. Test Ex. 1 | Comp Test Ex. 2 | Comp. Test Ex. 3 | Comp. Test Ex. 4 | Comp. Test Ex. 5 | Comp. Test Ex. 6 | Comp. Test Ex. 7 | Comp. Test Ex. 8 | Comp. Test Ex. 9 |
|---|---|---|---|---|---|---|---|---|---|---|---|---|---|
| Product distribution/wt % | | | | | | | | | | | | | |
| Dry gas | 1.23 | 1.35 | 1.19 | 1.27 | 2.25 | 2.37 | 2.09 | 1.79 | 1.89 | 1.97 | 2.05 | 1.25 | 2.6 |
| Liquefied gas | 17.83 | 17.41 | 17.19 | 17.45 | 10.17 | 10.87 | 14.35 | 15.45 | 15.27 | 15.15 | 14.35 | 17.82 | 11.3 |
| Coke | 1.09 | 1.02 | 0.83 | 1.14 | 4.46 | 4.65 | 3.1 | 1.98 | 2.4 | 2.79 | 3.01 | 1.15 | 3.9 |
| Gasoline | 57.95 | 57.37 | 58.41 | 57.52 | 45.24 | 45.78 | 46.83 | 52.03 | 51.58 | 52.65 | 47.83 | 57.65 | 45.1 |
| Diesel oil | 20.25 | 21.31 | 20.95 | 20.9 | 34.76 | 34.02 | 30.51 | 26.95 | 26.81 | 25.37 | 30.51 | 20.45 | 34.5 |
| Heavy oil | 1.65 | 1.54 | 1.43 | 1.72 | 3.12 | 2.31 | 3.12 | 1.8 | 2.05 | 2.07 | 2.25 | 1.68 | 2.6 |
| Total | 100 | 100 | 100 | 100 | 100 | 100 | 100 | 100 | 100 | 100 | 100 | 100 | 100 |
| Content of BTX aromatics in gasoline/% | 72.65 | 73.81 | 72.15 | 72.40 | 57.15 | 58.11 | 57.21 | 62.36 | 62.05 | 72.11 | 59.48 | 69.52 | 54.69 |
| Yield of BTX aromatics/wt % | 42.10 | 42.34 | 42.14 | 41.65 | 25.85 | 26.60 | 26.79 | 32.45 | 32.01 | 37.97 | 28.45 | 40.08 | 24.67 |
| Effective conversion rate of LCO/% | 75.78 | 74.78 | 75.6 | 74.97 | 55.41 | 56.65 | 61.18 | 67.48 | 66.85 | 67.8 | 62.18 | 75.47 | 56.4 |
| Propylene yield/% | 5.53 | 5.52 | 5.37 | 5.38 | 2.22 | 2.39 | 3.05 | 3.51 | 3.39 | 4.78 | 3.28 | 3.65 | 2.44 |
| Propylene concentration in liquefied gas/% | 31.02 | 31.71 | 31.23 | 30.83 | 21.83 | 21.95 | 21.25 | 22.72 | 22.20 | 31.55 | 22.85 | 20.48 | 21.59 |

As can be seen from the results listed in Tables 2 and 4, the catalytic cracking catalyst provided in the present application shows a high hydrothermal stability, a significantly lower coke selectivity, and a significantly higher gasoline yield. Besides, the yield of BTX (benzene+toluene+xylene) in the gasoline is greatly improved, the propylene yield is improved and the liquefied gas product obtained has a high propylene concentration.

The preferred embodiments of the present application have been described in detail above, but the present application is not limited to the specific details in the above-described embodiments, and various modifications can be made to the technical solutions of the present application without departing from the inventive concept of the present application. All such modifications are intended to be covered by the present application.

It should be further noted that the specific technical features described hereinabove in particular embodiments may be combined in any suitable manner without contradiction. For brevity, those potential combinations are not described herein individually. In addition, any combination of the various embodiments of the present application may be made as long as it does not deviate from the spirit of the present application, and such combinations should also be regarded as a part of the disclosure of the present application.

The invention claimed is:

1. A modified Y-type molecular sieve, having a rare earth content of about 4% to about 11% by weight on the basis of the oxide, a phosphorus content of about 0.05% to about 10% by weight on the basis of $P_2O_5$, a sodium content of no more than about 0.5% by weight on the basis of sodium oxide, a gallium content of about 0.1% to about 2.5% by weight on the basis of gallium oxide, and a zirconium content of about 0.1% to about 2.5% by weight on the basis of zirconia, based on the weight of the modified Y-type molecular sieve on a dry basis, wherein the modified Y-type molecular sieve has a total pore volume of about 0.36 mL/g to about 0.48 mL/g, a percentage of a pore volume of secondary pores having a pore size of 2-100 nm relative to the total pore volume of about 20% to about 40%,
a lattice constant of about 2.440 nm to about 2.455 nm, a lattice collapse temperature of not lower than about 1060° C., a percentage of non-framework aluminum content to the total aluminum content of no more than about 10%, and a ratio of B acid to L acid in the strong acid content of the modified Y-type molecular sieve of no less than about 3.5.

2. The modified Y-type molecular sieve according to claim 1, wherein the modified Y-type molecular sieve has one or more of the following characteristics:
a percentage of the pore volume of secondary pores having a pore size of 2-100 nm relative to the total pore volume of the modified Y-type molecular sieve of about 28% to about 38%;
a percentage of non-framework aluminum content relative to the total aluminum content of the modified Y-type molecular sieve of about 5% to about 9.8%;
a framework silica-alumina ratio of the modified Y-type molecular sieve of about 7 to about 14, calculated on the basis of $nSiO_2/n(Al_2O_3)$;
a lattice collapse temperature of the modified Y-type molecular sieve of about 1065° C. to about 1085° C.;
a ratio of B acid to L acid in the strong acid content of the modified Y-type molecular sieve of about 3.5 to about 6.5, as determined by the pyridine adsorption infrared spectroscopy at 350° C.;
a relative crystallinity of the modified Y-type molecular sieve of about 70% to about 80%; and/or
a relative crystallinity retention of the modified Y-type molecular sieve of about 38% or more, as determined by XRD after aging at 800° C. in 100% steam atmosphere for 17 hours.

3. The modified Y-type molecular sieve according to claim 1, wherein the rare earth content is about 4.5% to about 10%, the phosphorus content is about 0.5% to about 5%, the sodium content is about 0.05% to about 0.3%, the gallium content is about 0.2% to about 2%, and the zirconium content of about 0.5% to about 2%, the lattice constant is about 2.442 nm to about 2.451 nm; and the framework silica-alumina ratio is about 8.5 to about 12.6.

4. The modified Y-type molecular sieve according to claim 3, wherein the rare earth comprises a rare earth element selected from the group consisting of La, Ce, Pr, Nd, and any combination thereof.

5. A method for the preparation of a modified Y-type molecular sieve according to claim 1, comprising the steps of:
(1) contacting a NaY molecular sieve with a rare earth salt solution for ion-exchange reaction to obtain an ion-exchanged molecular sieve;
(2) subjecting the ion-exchanged molecular sieve to roasting at a temperature of about 350° C. to about 480° C. in an atmosphere comprising about 30 vol % to about 90 vol % of steam for about 4.5 hours to about 7 hours to obtain a molecular sieve undergone a mild hydrothermal ultra-stabilization treatment;
(3) subjecting the molecular sieve to a mild hydrothermal ultra-stabilization treatment to gas phase ultra-stabilization by contacting and reacting with gaseous $SiCl_4$ to obtain a gas phase ultra-stabilized molecular sieve;
(4) subjecting the gas phase ultra-stabilized molecular sieve to an acid treatment by contacting with an acid solution to obtain an acid-treated molecular sieve;
(5) subjecting the acid-treated molecular sieve to phosphorus modification by contacting with a phosphorus compound to obtain a phosphorus-modified molecular sieve; and
(6) subjecting the phosphorus-modified molecular sieve to a modification treatment by contacting with gallium and zirconium in a solution, and then to calcination, to obtain the modified Y-type molecular sieve.

6. The method according to claim 5, wherein the ion-exchange reaction is conducted under the following conditions:
a temperature of about 15° C. to about 95° C., a reaction time of about 30 min to about 120 min, and a weight ratio of the NaY molecular sieve, the rare earth salt and water of about 1:(0.01-0.18):(5-20).

7. The method according to claim 5, wherein the ion-exchanged molecular sieve has a lattice constant of about 2.465 nm to about 2.472 nm, a rare earth content of about 4.5% to about 13% by weight on the basis of the oxide, and a sodium content of about 4.5% to about 9.5% by weight on the basis of sodium oxide.

8. The method according to claim 5, wherein the rare earth salt is rare earth chloride or rare earth nitrate.

9. The method according to claim 5, wherein in the step (2), the ion-exchanged molecular sieve is subjected to roasting at a temperature of about 380° C. to about 460° C. in an atmosphere comprising about 40 vol % to about 80 vol % of steam for about 5 hours to about 6 hours.

10. The method according to claim 5, wherein, in the step (3), the weight ratio of the $SiCl_4$ to the molecular sieve undergone a mild hydrothermal ultra-stabilization treatment on a dry basis is about (0.1-0.7):1, the reaction temperature is about 200° C. to about 650° C., and the reaction time is about 10 min to about 5 hours.

11. The method according to claim 5, wherein in the step (4), the acid treatment is conducted a temperature of about 80° C. to about 99° C. for about 1 hour to about 4 hours, with the acid solution comprising an acid that is an organic acid, an inorganic acid, or a mixture thereof, and at a weight ratio of the acid in the acid solution, water in the acid solution, and the gas phase ultra-stabilized molecular sieve on a dry basis of about (0.001-0.15):(5-20):1.

12. The method according to claim 11, wherein the acid treatment of the step (4) further comprises: contacting the gas phase ultra-stabilized molecular sieve first with an inorganic acid solution, and then with an organic acid solution;
wherein the contacting with the inorganic acid solution is conducted under the following conditions: a contact time of about 60 min to about 120 min, a contact temperature of about 90° C. to about 98° C., and a weight ratio of the inorganic acid in the inorganic acid solution, water in the inorganic acid solution, and the gas phase ultra-stabilized molecular sieve on a dry basis of about (0.01-0.05):(5-20):1; and
the contacting with the organic acid solution is conducted under the following conditions: a contact time of about 60 min to about 120 min, a contact temperature of about 90° C. to about 98° C., and a weight ratio of the organic acid in the organic acid solution, water in the organic acid solution, and the gas phase ultra-stabilized molecular sieve on a dry basis of about (0.02-0.1):(5-20):1.

13. The method according to claim 11, wherein the organic acid is selected from the group consisting of oxalic acid, malonic acid, succinic acid, methyl succinic acid, malic acid, tartaric acid, citric acid, salicylic acid, and any combination thereof; and/or
the inorganic acid is selected from the group consisting of phosphoric acid, hydrochloric acid, nitric acid, sulfuric acid, and any combination thereof.

14. The method according to claim 5, wherein the phosphorus compound is selected from the group consisting of phosphoric acid, ammonium phosphate, ammonium dihydrogen phosphate, diammonium hydrogen phosphate, and combinations thereof.

15. The method according to claim 5, wherein the step (6) further comprises: mixing the phosphorus-modified molecular sieve homogeneously with an aqueous solution containing a gallium salt and a zirconium salt, and then standing at about 15° C. to about 40° C. for about 24 hours to about 36 hours, wherein the weight ratio of the gallium in the aqueous solution containing a gallium salt and a zirconium salt calculated on the basis of gallium oxide, the zirconium in the aqueous solution containing a gallium salt and a zirconium salt calculated on the basis of zirconia, and the phosphorus-modified molecular sieve on a dry basis is about (0.001-0.025):(0.001-0.025):1, and the weight ratio of water in the aqueous solution to the phosphorus-modified molecular sieve on a dry basis is about (2-3):1.

16. The method according to claim 5, wherein calcination in the step (6) is carried out under the following conditions: a calcination temperature of about 450° C. to about 600° C. and a calcination time of about 2 hours to about 5 hours.

17. The method according to claim 5, wherein the step (5) further comprises: contacting and reacting the acid-treated molecular sieve with a solution containing a phosphorus compound at a temperature of about 15° C. to about 100° C. for about 10 min to about 100 min, wherein the weight ratio of the phosphorus in the phosphorus compound-containing solution calculated on the basis of $P_2O_5$, water in the phosphorus compound-containing solution, and the acid-treated molecular sieve is about (0.0005-0.10):(2-5):1.

18. A catalytic cracking catalyst, comprising about 10% to about 50% by weight of a modified Y-type molecular sieve, about 10% to about 40% by weight of an alumina binder calculated on the basis of alumina, and about 10% to about 80% by weight on a dry basis of clay, based on the weight of the catalyst on a dry basis, wherein the modified Y-type molecular sieve is a modified Y-type molecular sieve according to claim 1.

19. The catalytic cracking catalyst of claim 18, wherein the clay is selected from the group consisting of kaolin, hydrated halloysite, montmorillonite, diatomaceous earth, halloysite, saponite, rectorite, sepiolite, attapulgite, hydrotalcite, bentonite, and combinations thereof; and/or the alumina binder is selected from the group consisting of alumina, hydrated alumina, aluminum sol, and combinations thereof.

20. A method for catalytic cracking of hydrocarbon, comprising contacting a hydrocarbon feedstock with a catalytic cracking catalyst comprising the modified Y-type molecular sieve of claim 1 under catalytic cracking conditions.

21. The method for catalytic cracking of hydrocarbon of claim 20, wherein the hydrocarbon feedstock is a hydrogenated light cycle oil (LCO).

\* \* \* \* \*